United States Patent
Welch et al.

(10) Patent No.: US 11,538,009 B2
(45) Date of Patent: Dec. 27, 2022

(54) BEVERAGE VENDING DEVICE NETWORKING

(71) Applicant: The Coca-Cola Company, Atlanta, GA (US)

(72) Inventors: Dick P. Welch, Marietta, GA (US); Ed Teller, Acworth, GA (US); Michael Edward Hopkins, Atlanta, GA (US); Cindy Pang, Atlanta, GA (US); Mark Adams, Buford, GA (US); Kyusang Kim, Richmond, TX (US)

(73) Assignee: The Coca-Cola Company, Atlanta, GA (US)

( * ) Notice: Subject to any disclaimer, the term of this patent is extended or adjusted under 35 U.S.C. 154(b) by 378 days.

(21) Appl. No.: 16/499,298

(22) PCT Filed: Mar. 29, 2018

(86) PCT No.: PCT/US2018/025088
§ 371 (c)(1),
(2) Date: Sep. 29, 2019

(87) PCT Pub. No.: WO2018/183642
PCT Pub. Date: Oct. 4, 2018

(65) Prior Publication Data
US 2021/0110365 A1    Apr. 15, 2021

Related U.S. Application Data

(60) Provisional application No. 62/478,805, filed on Mar. 30, 2017.

(51) Int. Cl.
*G06Q 20/18* (2012.01)
*G07F 9/00* (2006.01)
(Continued)

(52) U.S. Cl.
CPC .......... *G06Q 20/18* (2013.01); *G06Q 20/145* (2013.01); *G06Q 20/202* (2013.01); *G07F 9/002* (2020.05); *G07F 13/025* (2013.01); *G07F 13/065* (2013.01)

(58) Field of Classification Search
CPC .......................... G06Q 20/18; G06Q 20/145
(Continued)

(56) References Cited

U.S. PATENT DOCUMENTS 6,462,644 B1    10/2002 Howell et al.
2004/0114557 A1    6/2004 Bryan et al.
(Continued)

OTHER PUBLICATIONS

Authors::Asmita P. Bodhale: Beverages in Dispenser Machine According to Capsule Identification with Barcode; IEEE Conference Paper: Publication Date: Aug. 1, 2017 Electronic Publication Date: Sep. 11, 2018 Conference Start Date: Aug. 17, 2017 (Year: 2017).*

(Continued)

*Primary Examiner* — Hani M Kazimi
*Assistant Examiner* — Hatem M Ali

(57) ABSTRACT

In an example embodiment, a beverage vending device is provided that includes a network interface and one or more processors. The beverage vending device also includes a computer-readable tangible medium with instructions stored thereon that direct the one or more processors to establish contact with an available network and locate a second beverage vending device on the network. The computer-readable tangible medium also has instructions stored thereon that direct the one or more processors to establish contact with the second beverage vending device on the network, and communicate with the second beverage vending device via the network.

18 Claims, 13 Drawing Sheets

(51) Int. Cl.
*G06Q 20/14* (2012.01)
*G06Q 20/20* (2012.01)
*G07F 13/02* (2006.01)
*G07F 13/06* (2006.01)

(58) Field of Classification Search
USPC .......................................................... 705/35
See application file for complete search history.

(56) References Cited

U.S. PATENT DOCUMENTS

| | | | |
|---|---|---|---|
| 2006/0096997 A1* | 5/2006 | Yeo | G07F 5/18 221/9 |
| 2006/0167967 A1* | 7/2006 | Defosse | G07F 9/002 709/201 |
| 2009/0069932 A1* | 3/2009 | Rudick | G07F 13/065 700/239 |
| 2009/0157515 A1 | 6/2009 | Lafauci et al. | |
| 2009/0219140 A1 | 9/2009 | Guard et al. | |
| 2012/0152125 A1 | 6/2012 | Yoakim et al. | |
| 2016/0363921 A1 | 12/2016 | Martindale et al. | |

OTHER PUBLICATIONS

Authors: G. Satya Shankaraiah et al ; Android based fluid dispensing and blending system automation; Publication Date: Dec. 1, 2014 Electronic Publication Date: Sep. 2, 2015 Conference Start Date: Dec. 18, 2014 (Year: 2014).*

Authors::Asmita P. Bodhale: Beverages in Dispenser Machine According to I IEEE Conference Paper: Publication Date: Aug. 1, 2017 Electronic Publication Date: Sep. 11, 2018 (Year: 2018).*

Authors: G. Satya Shankaraiah et al ; Android based fluid dispensing and blending system automation; Publication Date: Dec. 1, 2014; Electronic Publication Date: Sep. 2, 2015 (Year: 2015).*

Kang, Hee Gok; International Search Report; dated Jul. 10, 2018; pp. 1-4; Korean Intellectual Property Office; Daejeon, Republic of Korea.

* cited by examiner

| Beverage Vending Device ID 904 | Cartridge / Ingredient ID 906 | Percent Remaining 908 | Errors 910 | Cleaning Status 912 | Work Order Status 914 | Other Date 916 |
|---|---|---|---|---|---|---|
| ZPL33424 | 06 | 0.32 | XYZ02 | | | |

BEVERAGE VENDING DEVICE NETWORKING

RELATED APPLICATIONS

This present application claims priority to and benefit of International PCT Application No. PCT/US2018/025088, filed Mar. 29, 2018, and U.S. Provisional Application No. 62/478,152, filed Mar. 29, 2017, and entitled "BEVERAGE VENDING DEVICE NETWORKING," which are hereby incorporated by reference in their entireties for all purposes.

TRADEMARKS

COCA-COLA® is a registered trademark of The Coca-Cola Company, Atlanta, Ga., U.S.A. Other names, symbols, designs, or logos used herein may be registered trademarks, trademarks or product names of The Coca-Cola Company or other companies.

BACKGROUND

It can often be desirable to control various aspects of dispensed and/or vended drinks in order to, for example, control costs, simplify compliance with recent government regulations (i.e. limits on free refills), etc.

Several control techniques already exist in the prior art. For instance, approaches utilizing radio-frequency identification (RFID) technologies have been commercialized. However costs associated with RFID tags and cups fitted with RFID chips—both in terms of money and cumbersome interactions with third party RFID technology suppliers—have proven to be unattractive.

Similarly, with regard to approaches using serialized bar codes, a threat of forgery of the bar codes is ever present.

The above descriptions and examples are not admitted to be prior art by virtue of their inclusion in this section.

SUMMARY

In an example embodiment, a beverage vending device is provided that includes a network interface and one or more processors. The beverage vending device also includes a computer-readable tangible medium with instructions stored thereon that direct the one or more processors to establish contact with an available network and locate a second beverage vending device on the network. The computer-readable tangible medium also has instructions stored thereon that direct the one or more processors to establish contact with the second beverage vending device on the network, and communicate with the second beverage vending device via the network.

In another example embodiment, a computer-readable tangible medium configured for use with a first beverage vending device is provided. The computer-readable tangible medium includes instructions stored thereon that, when executed, direct a processor to establish contact between the first beverage vending device and a second beverage vending device, and facilitate communication between the first beverage vending device and the second beverage vending device.

In yet another example embodiment, a beverage vending device is provided including a network interface and one or more processors. The beverage vending device also includes a computer-readable tangible medium with instructions stored thereon that, when executed, direct the one or more processors to locate a second beverage vending device, and establish direct communication with the second beverage vending device.

This summary is not intended to identify key or essential features of the claimed subject matter, nor is it intended to be used as an aid in limiting the scope of the claimed subject matter.

Other features of the current disclosure will become apparent to those skilled in the art upon review of the following drawings, the detailed description, and the appended claims.

BRIEF DESCRIPTION OF THE DRAWINGS

Illustrative embodiments will be described referring to the accompanying drawings, wherein like numerals denote like elements.

DETAILED DESCRIPTION

In the following description, numerous details are set forth to provide an understanding of some embodiments of the present disclosure. However, it will be understood by those of ordinary skill in the art that the systems and/or methodologies may be practiced without these details and that numerous variations or modifications from the described embodiments may be possible.

As described herein, various techniques and technologies associated with beverage vending device networking can be used, for example, to network two or more beverage vending devices together so that they can communicate with one another directly and/or via a server. In one possible implementation, encryption/decryption technologies can be used to control the pouring of a beverage to a consumer at any of the beverage vending devices.

In some implementations, it may be desirable to have communication means between beverage vending devices to better serve customers and to ensure compliance where multiple beverage vending devices are available. Moreover, in various implementations, it may be desirable to have a network of beverage vending devices in order to facilitate other transactional operations, such as updates, inventory, maintenance, content changes, ordering, etc., associated with one or more of the beverage vending devices.

Example Techniques, Processes, Etc.

Figure 1:
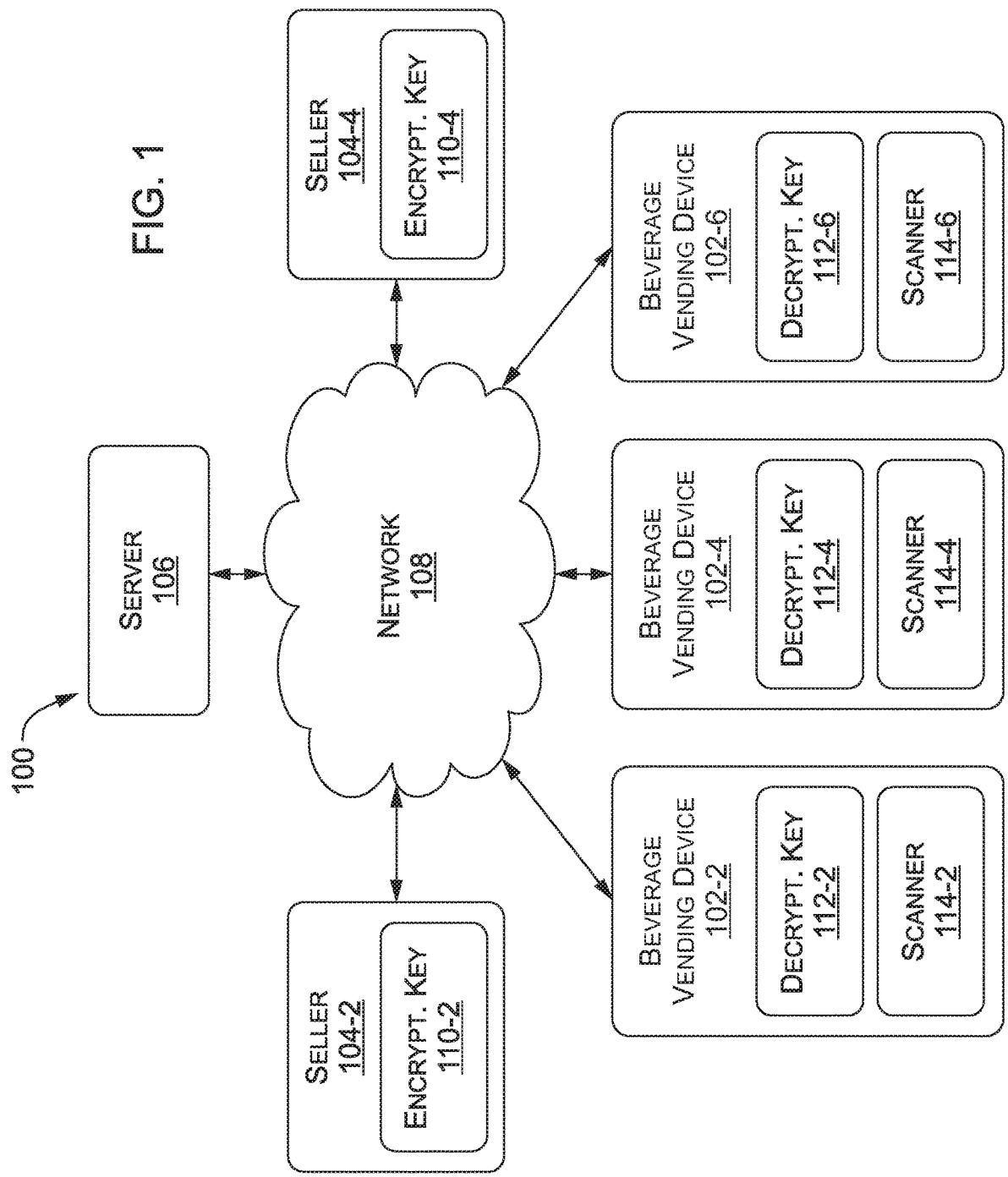
FIG. 1 illustrates an example configuration of one or more beverage vending devices and one or more sellers in one possible embodiment of beverage vending device networking.

FIG. 1 illustrates an example configuration 100 of one or more beverage vending devices 102 and one or more sellers 104 in one possible embodiment of beverage vending device networking. Even though three beverage vending devices 102-2, 102-4, 102-6 and two sellers 104-2, 104-4 are illustrated in FIG. 1, it will be understood that more or less beverage vending devices 102 and/or sellers 104 can also be present.

Beverage vending devices 102 can comprise any devices configured to dispense and/or vend beverages to consumers including, for example, beverage dispensers (i.e. dispensers of fountain beverages, etc.), vending machines, coolers, and so on. Further, beverage vending devices 102 can include one or more computing and/or programmable devices enabling beverage vending devices 102 to run programs and interact with, manipulate, store, transmit, etc., various forms of data.

Sellers 104-2, 104-4 can include any entity wishing to sell a beverage to a consumer and/or dispense a beverage to a consumer via beverage vending devices 102-2, 102-4, 102-6. Thus sellers 104-2, 104-4 can include restaurants, snack bars, etc.

In one possible implementation, configuration 100 can represent a dispersed serving area, such as a food court, a theme park, a sports venue (such as a stadium, an arena, a ball park, etc.), a theater, a cruise ship, a campus, and so on. In one possible implementation, such as the case of a food court, sellers 104 can be different restaurants, and the plurality of beverage vending devices 102 can be various self-serve and crew served beverage dispensers throughout the food court. In another possible implementation, such as the case of a theater, sellers 104 can all represent the same entity (i.e. the theater) and the plurality of beverage vending devices 102 can be various self-serve and crew served beverage dispensers throughout the theater.

In some possible implementations, one or more servers 106 can also be present in configuration 100. Server 106 can collect information from sellers 104 and beverage vending devices 102, as well as transmit information, such as, for example updates, etc., to sellers 104 and beverage vending devices 102. For example, in one possible embodiment, beverage vending devices 102, sellers 104, and/or server 106 can communicate information amongst themselves by sending packets over a network 108. The packets can include log files to update settings, etc., and/or instructions to execute various programs, such as programs installed on beverage vending devices 102. In one possible aspect, such log files can be sent by beverage vending devices 102 to server 106 in any fashion known in the art including in real-time, at one or more predetermined times (e.g. nightly), when an action of interest takes place, when an appropriate query is made, etc. In a similar fashion, updates and/or instructions can be sent from server 106 to sellers 104 and/or beverage vending devices 102 in any fashion known in the art including continuously, at predetermined times (e.g. nightly), when an action of interest takes place, when an appropriate query is made, etc.

Server 106 can comprise anything known in the art that can send and receive information and instructions to sellers 104 and beverage vending devices 102, including a local computer or computer system, a point of sale (POS) computing device, etc.

As illustrated, beverage vending devices 102-2, 102-4, 102-6, sellers 104-2, 104-4 and server 106 (if present) can be connected via network 108. It will be understood that network 108 can include any technology known in the art capable of allowing communication between beverage vending devices 102-2, 102-4, 102-6, sellers 104-2, 104-4, server 106 (if present), and other present entities. This can include any wired and/or wireless technologies known in the art, including any possible combinations thereof.

For example, some or all of network 108 can be administered through an existing hot spot (such as a hot spot run by a seller 104). Alternately, or additionally, some or all of network 108 can include direct links between beverage vending devices 102-2, 102-4, 102-6, sellers 104-2, 104-4 and server 106 (if present) via Ethernet, fiber optic, and/or any other networking technologies known in the art (including, for instance, 4G, 5G, Bluetooth, cloud, near field communication (NFC) technologies, and so on).

In one possible implementation, network 108 can allow communication between server 106, all of beverage vending devices 102-2, 102-4, 102-6, and all of sellers 104-2, 104-4. In alternate embodiments, sellers 104-2, 104-4 can be connected to server 106 via network 108 without being connected to beverage vending devices 102-2, 102-4, 102-6. This can include configurations in which each of sellers 104-2, 104-4 is connected to server 106 without being connected to one another.

In other possible configurations, one or more of beverage vending devices 102-2, 102-4, 102-6 can be connected to server 106 via network 108 without being in communication with one or more of sellers 104-2, 104-4 via network 108. This can include instances where a first portion of network 108 enables communication between one or more of beverage vending devices 102-2, 102-4, 102-6 and server 106, and a second portion of network 108 enables communication between one or more of sellers 104-2, 104-4 and server 106. In one possible aspect, the first portion of network 108 and the second portion of network 108 can be separate entities.

In yet other possible configurations, beverage vending devices 102-2, 102-4, 102-6 can be connected directly to one another—such as in various peer to peer configurations—enabling beverage vending devices 102-2, 102-4, 102-6 to communicate directly with each other without intervention of other devices, such as server 106.

In one possible aspect, sellers 104-2, 104-4 can enable a consumer to request a beverage dispense from beverage vending devices 102-2, 102-4, 102-6 by transmitting an encrypted dispense string to the consumer. In such an aspect, sellers 104-2, 104-4 can use encryption keys 110-2, 110-4, respectively, to encrypt communications (such as dispense strings, for example), and beverage vending devices 102-2, 102-4, 102-6 can use one or more decryption keys 112-2, 112-4, 112-6 to decrypt the communications.

In one possible embodiment, encryption keys 110-2, 110-4 and decryption keys 112-2, 112-4, 112-6 can be transmitted to sellers 104-2, 104-4 and beverage vending devices 102-2, 102-4, 102-6 by server 106. Such transmissions can include updates of encryption keys 110-2, 110-4 and decryption keys 112-2, 112-4, 112-6 from server 106, and can happen in any manner desired, including at set intervals, on demand, etc.

In one possible implementation, once a dispense string has been encrypted, the encrypted dispense string can be transmitted to the consumer in the form of a machine-readable code, which the consumer can present for scanning at one or more of scanners 114-2, 114-4, 114-6 associated with beverage vending devices 102-2, 102-4, 102-6.

The machine-readable code can include anything known in the art, such as, for example, a code associated with a magnetic stripe, a one dimensional barcode, a two dimensional barcode, etc., and/or any combination thereof. This can include, for instance, a universal product code (UPC), a European article number (EAN) code; a code 39 barcode, a code 128 barcode, and interleafed 2 of 5 (ITF) barcode, a code 93 barcode, a codabar barcode, a GS1 databar barcode, a modified Plessey barcode, a quick response (QR) code barcode, a Datamatrix barcode, a PDF417 barcode, an Aztec barcode, etc.

The machine-readable code can be issued to the consumer through any technique known in the art. For example, the consumer can receive a cup on which the machine-readable code is printed/formed. Alternately, or additionally, the consumer can receive a receipt, coupon, giftcard, etc., on which the machine-readable-code is printed/formed. In one possible implementation, the machine-readable code on such a receipt, coupon, giftcard, etc., can be in the form of a sticker which can be affixed to a beverage container that the consumer can use to request the desired beverage from a beverage vending device 102. In yet another possible implementation, the machine-readable code can be accessed by the consumer via a handheld device (such as a mobile phone, a tablet, a laptop, etc.).

Scanners 114-2, 114-4, 114-6 can be located anywhere on beverage vending devices 102-2, 102-4, 102-6, with the possibility of each beverage vending device 102-2, 102-4, 102-6 having more than one scanner 114. Moreover, scanners 114-2, 114-4, 114-6 can include any scanning technologies known in the art configured to scan the machine-readable codes discussed above.

Figure 2:
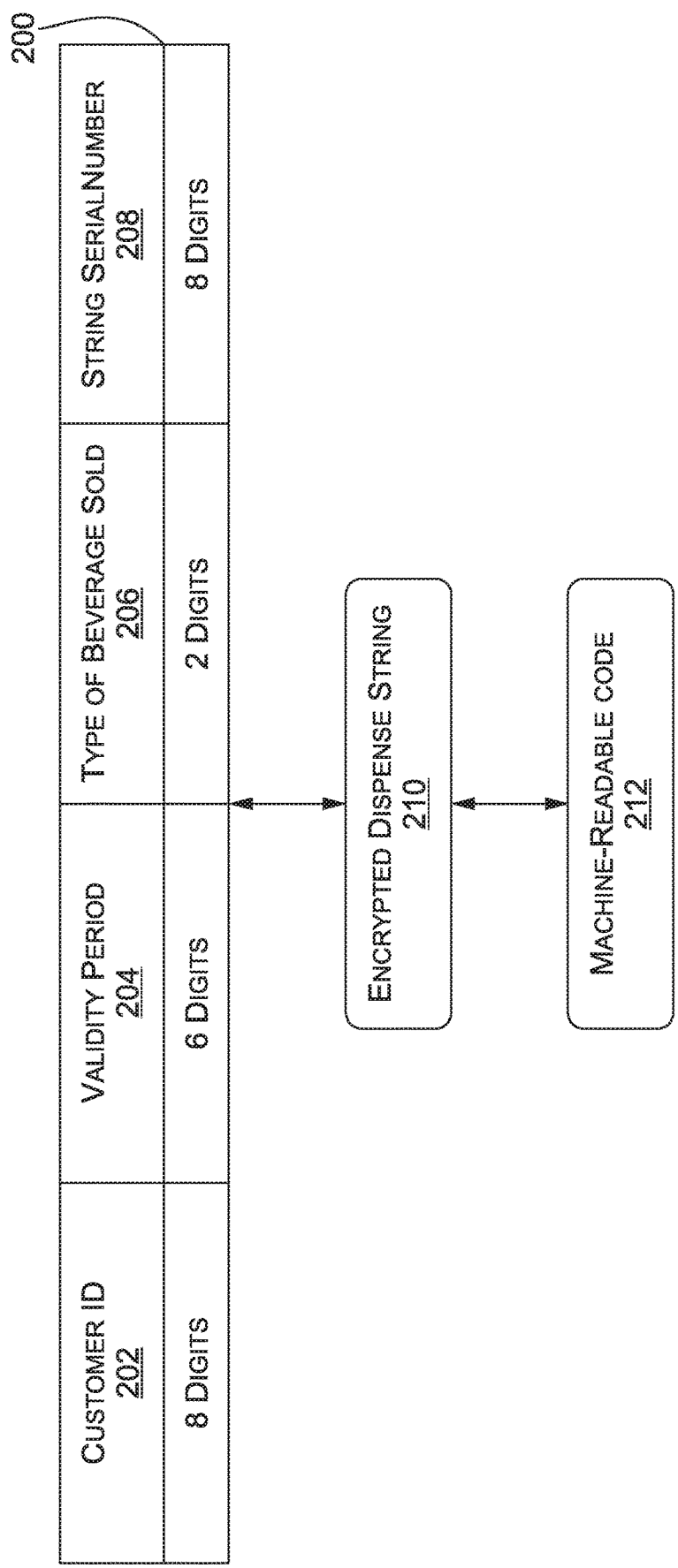
FIG. 2 illustrates an example dispense string in accordance with various embodiments of beverage vending device networking.

FIG. 2 illustrates an example dispense string 200 including information which can be meaningful to beverage vending devices 102-2, 102-4, 102-6 in accordance with various embodiments of beverage vending device networking. In one possible implementation, dispense string 200 can include a collection of blocks of information (such as numbers, letters, etc.), with each block having an associated meaning. As illustrated, dispense string 200 includes four blocks, namely a customer identifier (ID) 202, a validity period 204, a type of beverage sold 206, and a string serial number 208. It will be understood that more or less blocks, as desired, can be associated with dispense string 200, such that dispense string 200 can represent any variety of desired information.

It will also be understood that the number of digits of customer identifier (ID) 202, validity period 204, type of beverage sold 206, and string serial number 208 as illustrated in FIG. 2 represent one possible implementation. More or less digits can also be used for one or more of customer identifier (ID) 202, validity period 204, type of beverage sold 206, and string serial number 208, as desired.

Customer ID 202 can uniquely identify a seller 104. In the event that the seller 104 has several locations, customer ID 202 can be shared for all locations. Alternately different customer IDs 202 can be issued for each location of seller 104 and/or for multiple pre-chosen locations of seller 104 in a specific area, etc. Further, if desired, customer IDs 202 can be issued for individual salespeople, etc., associated with a seller 104.

Validity period 204 can include a date of sale, date of transfer, date of a beginning of validity, etc., of dispense string 200, and can be used to limit a duration of validity during which the consumer can use dispense string 200 to dispense a beverage from one or more of beverage vending devices 102-2, 102-4, 102-6. For example, in one possible implementation, by presenting dispense string 200 to a beverage vending device 102 the consumer may be allowed to get one or more beverage dispenses on a given date in validity period 204. In another possible implementation, the consumer may be allowed to get one or more beverage dispenses on any day in a range of dates indicated by all or part of validity period 204.

Type of beverage sold 206 can be used as future proofing for different pricing on different types of beverages (such as, for example, juice, tea, sparkling water, still water, etc.). For instance, if a consumer buys a beverage in a certain drink class (such as, for example, a soft drink), type of beverage sold 206 can indicate the specific brand/type of soft drink purchased, or the generic class of "soft drinks".

In one possible aspect, type of beverage sold 206 can be used to limit the consumer to beverage dispenses of only the beverage indicated in type of beverage sold 206. In other aspects, the consumer can be allowed to dispense other beverages with prices equal to and/or cheaper than the beverage indicated by type of beverage sold 206. For instance if the consumer purchased an expensive beverage category such as "juice", in one possible aspect, the consumer could be allowed to dispense cheaper beverage categories like "water", "flavored water", etc., in addition to juice.

String serial number 208 can be a unique indicator for a consumer (or a group of consumers, if desired). String serial number 208 can be used for a variety of purposes, including, for example, limiting dispenses to individual consumers.

In one possible implementation, an asymmetric encryption algorithm (such as the advanced encryption standard (AES) or any other algorithm known in the art) can be used to encrypt dispense string 200 to form an encrypted dispense string 210 (such as the encrypted dispense string described above) that can correspondingly be transformed into a machine-readable code 212 (such as the machine readable code described above) using any technique and/or technology known in the art, before dispense string 200 is passed to the consumer. In one possible implementation, giving a consumer an encrypted dispense string 210 in the form of machine-readable code 212, rather than simply giving the consumer the dispense string 200 in the form of machine-readable code 212, decreases the risk of anyone forging dispense string 200. In one possible embodiment, the machine-readable code 212 can be designed such that it becomes obfuscated (i.e. turns black, or otherwise becomes unreadable) once validity period 204 expires.

In one possible implementation, encryption and decryption of dispense string 200 can be accomplished using private and public keys. For example, encryption key 110-2 of seller 104-2 can be a private key, and decryption key 112-2 of beverage vending device 102-2 being used by a consumer can comprise a corresponding public key. It will be noted that the same public key can be made available to all beverage vending devices 102-2, 102-4, 102-6 in configuration 100.

By utilizing private and public keys in this manner, every seller 104 can produce secure machine-readable codes 212 for their consumers by encrypting dispense strings 200 and converting them into machine-readable codes 212. Machine-readable codes 212 can be scanned by scanners 114-2, 114-4, 114-6 in beverage vending devices 102-2, 102-4, 102-6 and the encrypted dispense strings 210 in machine-readable codes 212 can be decrypted into the original dispense strings 200.

For example, in one possible implementation, when seller 104-4 (such as a restaurant in a food court) sells or otherwise transfers a beverage to a consumer, seller 104-4 can provide the consumer with a machine-readable code 212 on a cup, receipt, gift card, coupon, email, text, etc. Machine-readable code 212 can comprise encrypted dispense string 210, including information such as a customer identifier (ID) 202, a validity period 204, a type of beverage sold 206, and a string serial number 208. Machine-readable code 212 can be preprinted (such as by manufacturers of cups used by seller 104-4) or it can be printed on demand at a computing device, such as a cash register.

Sales and/or transfers of beverages to customers can be made by sellers 104 using any methods known in the art, including through vending machines, via mobile pay plans associated with mobile phones, etc. Moreover, sales and/or transfers of beverages can include any controls known in the art. For example customers can choose among various features, including validity periods, types of beverages, numbers of refills, etc., that they wish to purchase.

After receiving machine-readable code 212 from seller 104-4 (or one of his agents), the consumer can proceed to one of beverage vending devices 102-2, 102-4, 102-6, where machine-readable code 212 can be scanned using one or more scanners 114 placed anywhere desired on a beverage vending device 102. Moreover, any software known in the art (such as that included in a scanning module) can be used to scan the machine-readable code 212 and produce encrypted dispense string 210.

For example, in one possible aspect, scanner 114 can be located proximate an area on beverage vending device 102 where a container will be placed by the consumer before a beverage dispense is requested. In such a scenario, machine-readable code 212 on the container can be conveniently scanned. In another possible aspect, scanner 114 can be placed near a user interface on beverage vending device 102, such that a consumer can easily place machine-readable code 212 proximate scanner 114.

Once machine-readable code 212 has been successfully scanned by scanner 114, and encrypted dispense string 210 has been accessed, beverage vending device 102 can decrypt encrypted dispense string 210 using a decryption key 112 to produce the underlying dispense string 200. In one possible implementation, any software known in the art (such as that included in a decryption module) can be used to perform such decryption.

For example, when dispense string 200 has been encrypted using a private key, a decryption module can decrypt encrypted dispense string 210 using a corresponding public key in its encryption/decryption key(s). In one possible aspect, a keyring of multiple public keys can be stored in the encryption/decryption key(s) such that the decryption module can try several public keys before finding the proper public key associated with the private key used to encrypt dispense string 200 into encrypted dispense string 210.

In one possible implementation, when the encrypted dispense string 210 is decrypted, customer ID 202 in dispense string 200 can be checked against the public key used for the decryption. In one possible aspect, if the public key is appropriate for customer ID 202 (i.e. customer ID 202 and the public key are both associated with seller 104-4), dispense string 200 can be processed as a valid string. If not, the next public key on the keyring can be checked until a valid customer ID 202-public key pair is found or until all the public keys have been tried.

If no match is found, encrypted dispense string 210 will not be decrypted (such as, for example, by a decryption module), and beverage vending device 102 can issue any desirable error message, such as, for example, that machine-readable code 212 is incorrect. Beverage vending device 102 can also display a try again strategy with instructions on how to reenter the machine-readable code 212. In one possible implementation, error messages, instructions, etc., can be displayed on a display associated with beverage vending device 102.

Alternately, if a valid customer ID 202-public key match is found, at least some of dispense string 200 may be used to determine if any restrictions stand in the way of a beverage dispense exist. Such restrictions can result in the alteration, or cancellation, of a requested beverage dispense.

Restrictions can include anything desirable to seller 104-4 and/or a person or entity administering beverage vending device 102 including, for example, restrictions on refills, restrictions on a time during which beverage dispenses can be made, restrictions on an amount of sweetener that can be dispensed to the consumer in a given period of time, restrictions on an amount of calories that can be dispensed to the consumer in a given period of time, restrictions on a type of beverage that can be dispensed to the consumer given the type of beverage purchased by the consumer (i.e. purchases of water may not be eligible for beverage dispenses of more expensive beverages like juices), etc. In one possible implementation, some or all of the restrictions applicable to a beverage vending device 102 can be stored in a memory area that holds, for example, restrictions. Moreover, the restrictions, and their limits and thresholds, etc., can be updated through communications between beverage vending devices 102-2, 102-4, 102-6 and one or more outside entities, including for example, server 106, sellers 104, etc.

In some jurisdictions, laws and/or regulations may exist stipulating a restriction that no refills be given of certain beverages. In another possible example, laws and/or regulations may exist stipulating restrictions associated with a maximum limit of calories and/or sugar that can be dispensed in one or more beverages to a consumer in a given time period. In yet another example, a restriction may exist regarding a validity of dispense string 200 (i.e. perhaps validity period 204 can allow the consumer to request a beverage dispense on a given calendar day, within a set number of hours of purchase from a seller 104, and/or any other time limit set by a seller 104 and/or the entity administering the beverage vending devices 102).

In one possible aspect, if a beverage dispense requested by a customer associated with dispense string 200 doesn't run afoul of any of the restrictions, a beverage dispense decision can be made to implement the requested beverage dispense from a beverage vending device 102. In another possible aspect, if the beverage dispense requested by a customer associated with dispense string 200 does run afoul of any of the restrictions, a beverage dispense decision can be made to either issue an error message and block the requested beverage dispense, or issue an error message and present the consumer with a few options (if any are possible) on how to vary the requested beverage dispense to avoid running afoul of the restriction(s).

In still another possible aspect, if the beverage dispense requested by a customer associated with dispense string 200 runs afoul of any of the restrictions, a beverage dispense decision can be made automatically to implement a beverage dispense that complies with the restrictions. For example, if a consumer wishes to get a refill of a beverage, but that refill would result in a dispense of more sugar to the consumer than is allowed by a local regulation in a given period of time, a beverage dispense decision can be made to dispense an amount of the requested beverage into the consumer's container such that the total amount of sugar dispensed to the consumer over the given period of time does not exceed a threshold spelled out in the restriction. In one possible implementation, any software known in the art (including a dispense decision module) can be used to make such dispense decisions.

In one possible implementation, beverage vending devices 102-2, 102-4, 102-6, in configuration 100 can communicate with one another (either directly and/or through server 106) information regarding a consumer's beverage dispenses (i.e. beverage dispenses associated with a given string serial number 208). Such synchronization of beverage vending devices 102-2, 102-4, 102-6 can be done periodically (i.e. on a set schedule), can be triggered when a beverage dispense is completed to a consumer associated with a dispense string 200 at beverage vending devices 102-2, 102-4, 102-6, or can be implemented using any other methodologies known in the art. The synchronization can be conducted over network 108, and/or any other manners known in the art. Such synchronization efforts can be implemented using any software in the art including, for example, through use of a database querying module.

For example, if the present date is within validity period 204, and no restrictions exist blocking dispense of a beverage being requested (i.e. the beverage being requested is authorized for dispense given the type of beverage sold 206, no restrictions against refills and/or sweetener levels exist, etc.), a dispense decision can be made authorizing a dispense of the beverage being requested, and the beverage can be dispensed to the consumer. In one possible aspect, as noted above, information associated with the beverage dispense resulting from the dispense decision can then be communicated to other beverage vending devices 102-2, 102-4, 102-6 in configuration 100 for future reference in case the dispense string 200 is presented at another beverage vending device 102-2, 102-4, 102-6 in configuration 100 in the future. In one possible aspect, previous beverage dispense information like this can be stored in previous dispense information stored in memory on, for example, one or more beverage vending devices 102 and/or server 106.

In one possible implementation, a beverage vending device 102 can query one or more databases for previous dispense information associated with dispense string 200. This can include querying for previous dispense information on the beverage vending device 102 at which the consumer is requesting a beverage dispense, and/or querying previous dispense information associated with dispense string 200 from other beverage vending devices 102-2, 102-4, 102-6 in configuration 100 and/or querying for previous dispense information associated with dispense string 200 on server 106.

In one possible embodiment, beverage vending devices 102-2, 102-4, 102-6 can use any technologies known in the art (including for example, Wifi and/or network 108) to exchange data regarding previous dispense information associated with dispense string 200 (such as customer ID 202). This can include, for example, an amount of beverages already dispensed in accordance with dispense string 200 (and when), etc. Using such an approach, a total volume of beverages poured using dispense string 200 within a given time period at any of beverage vending devices 102-2, 102-4, 102-6 in configuration 100 can be accessed. This information can be used to comply with any existing restrictions regardless of which beverage vending devices 102-2, 102-4, 102-6 in configuration 100 were previously used by the consumer presenting dispense string 200.

Figure 3:
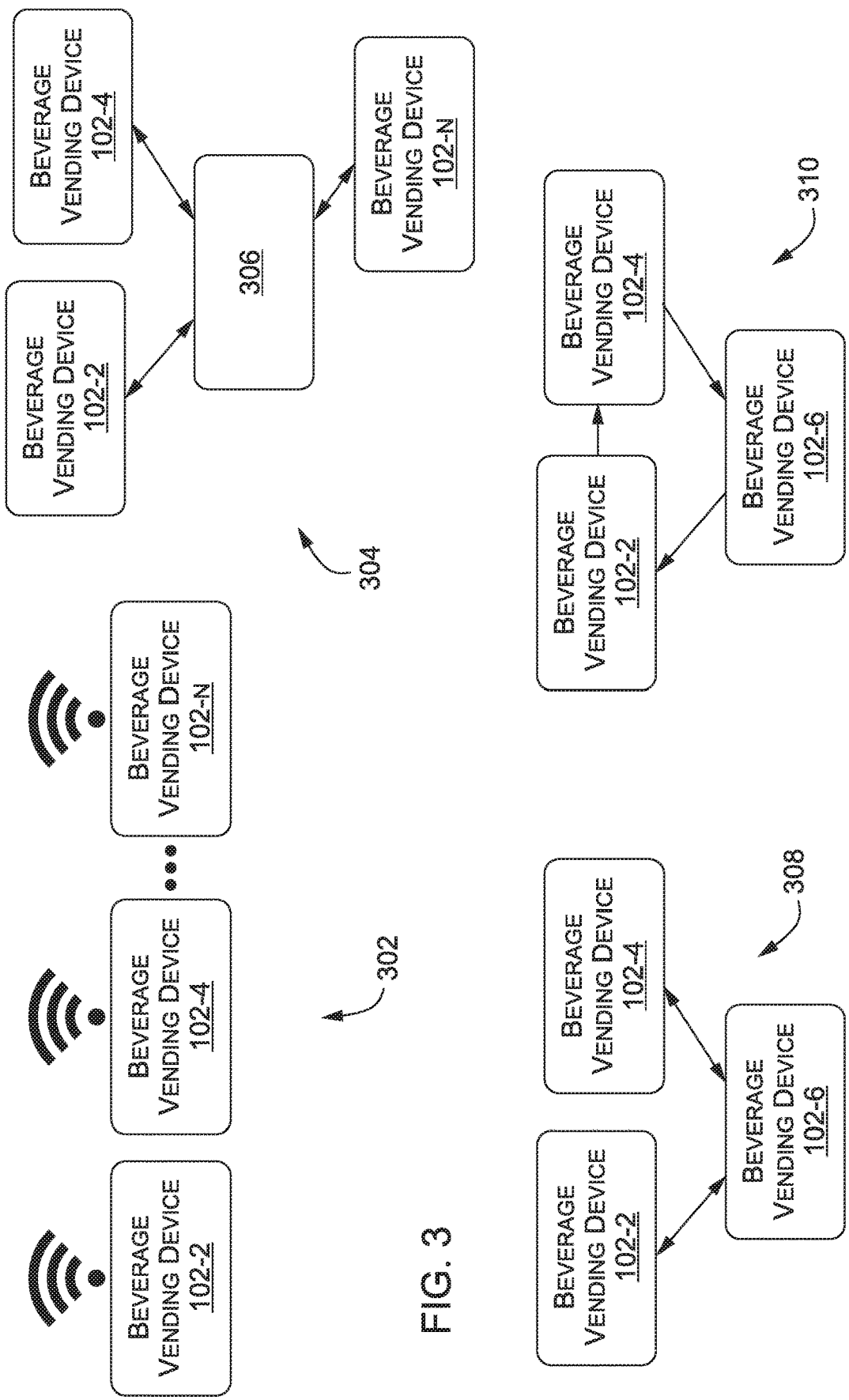
FIG. 3 illustrates several examples of peer to peer configurations that can be used to connect beverage vending devices in accordance with various embodiments of beverage vending device networking.

FIG. 3 illustrates several example peer-to-peer configurations that can be used in configuration 100 in accordance with various embodiments of beverage vending device networking. For example, in a broadcast configuration 302, any desired number of beverage vending devices 102 can be connected wirelessly using any wireless technologies in the art. In one possible implementation, any given beverage vending device 102 can broadcast to all beverage vending devices 102 or any select subset of beverage vending devices 102 in broadcast configuration 302. For example, beverage vending device 102-2 can broadcast to all beverage vending devices 102 in configuration 302, or beverage vending device 102-2 can broadcast to beverage vending device 102-N.

In another possible configuration 304, any desired number of beverage vending devices 102 can be connected in a star configuration through a hub 306. Hub 306 can include any device configured to allow communication between beverage vending devices 102 (including implementations in which hub 306 is itself a beverage vending device 102), and connections between the beverage vending devices 102 and hub 306 can be conducted using any communication technologies known in the art, including wireless technologies, wired technologies, and any combinations thereof.

In yet another possible configuration, any desired number of beverage vending devices 102 can be connected through a master/slave configuration 308. For example, two or more slave beverage vending devices 102 can be connected to a master beverage vending device 102-6. As many slave beverage vending devices 102 as desired can be connected to master beverage vending device 102-6, and connections between slave beverage vending devices 102 and master beverage vending device 102-6 can take the form of any communication technologies known in the art, including wireless technologies, wired technologies, and any combinations thereof.

In still another possible configuration, any desired number of beverage vending devices 102 can be connected through a ring configuration 310. For example, three or more beverage vending devices 102 can be connected to one another directly or via an intermediate beverage vending device 102. For example, beverage vending device 102-2 can communicate directly with beverage vending device 102-4 and indirectly with beverage vending device 102-6 via beverage vending device 102-4. Any communication technologies known in the art can be used to connect beverage vending devices 102 in ring configuration 310, including wireless technologies, wired technologies, and any combinations thereof.

It will also be understood that the above configurations 302, 304, 308, 310 can be combined in any manners possible in configuration 100.

Figure 4:
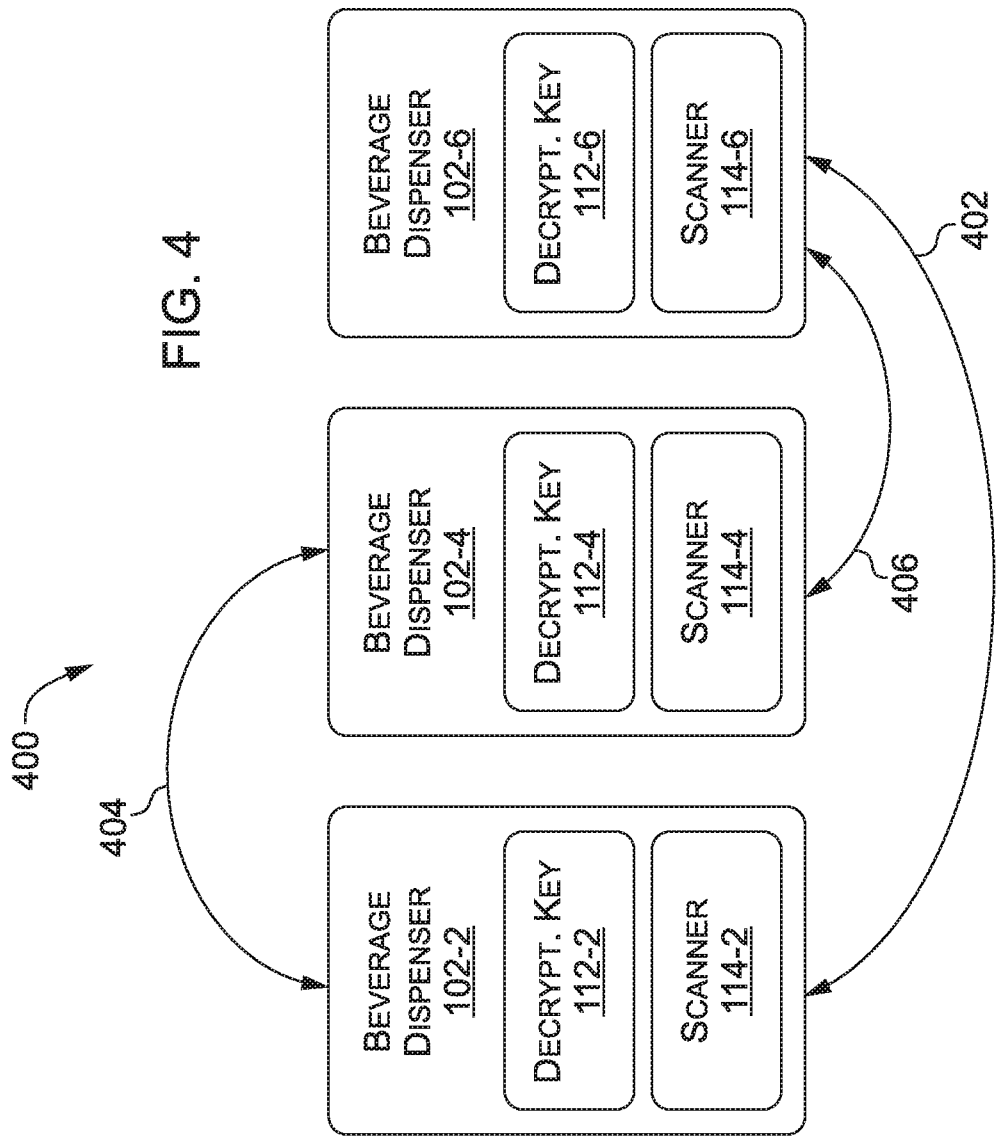
FIG. 4 illustrates a possible hybrid peer to peer configuration that can be used to connect beverage vending devices in accordance with various embodiments of beverage vending device networking.

FIG. 4 illustrates one such possible combination of configurations. As illustrated, one or more beverage vending devices 102 can be placed in communication with one or more other beverage vending devices 102 in a configuration 400. This can include direct connections between all beverage vending devices 102 in the group (as illustrated), and/or one or more indirect connections in any way possible between beverage vending devices 102. For instance, instead of (or in addition to) being directly coupled to beverage vending device 102-6 via a direct connection 402, beverage vending device 102-2 can be connected to beverage vending device 102-6 via beverage vending device 102-4 (such as, for example, in a hub and/or master/slave configuration), through connections 404 and 406. In a similar manner, in one possible implementation, all of beverage vending devices 102 in configuration 400 can be connected to server 106 (if present) either directly or indirectly, such as through one or more intervening beverage vending devices 102. Connections 402-406 can include any wired and/or wireless technologies known in the art, including any possible combination thereof.

With reference to FIGS. 1-4, in operation, a consumer desiring a beverage from one of beverage vending devices 102 could be granted access to the desired beverage by one of sellers 104. This could be implemented through any sort of transaction known in the art including, for example, a sale, a redemption of a coupon, etc. Access to the beverage could be granted by seller 104 (and/or an authorized associate of the seller) in a variety of ways, including, for example, via issuance of machine-readable code 212 to the consumer as described above.

In one possible implementation, the machine-readable code 212 can comprise dispense string 200 encoded into encoded dispense string 210 using an encryption key 110, which can be decoded at a beverage vending device 102 using a corresponding decryption key 112 associated with encryption key 110 and decryption key 112 can be any such keys known in the art including, for example, a private key and a public key, respectively.

Figure 5:
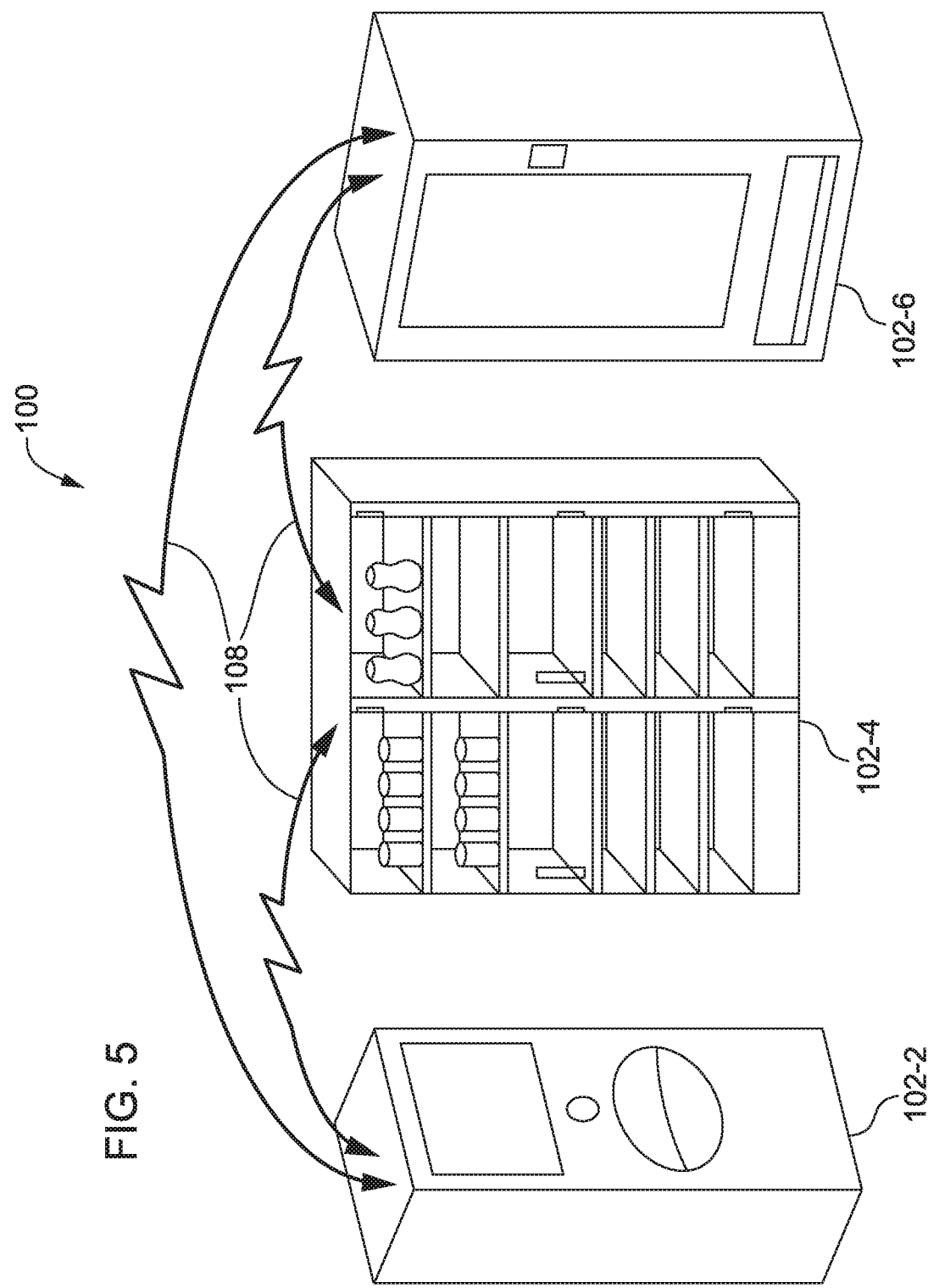
FIG. 5 illustrates an example of communication between beverage vending devices in accordance with various embodiments of beverage vending device networking.
Figure 6:
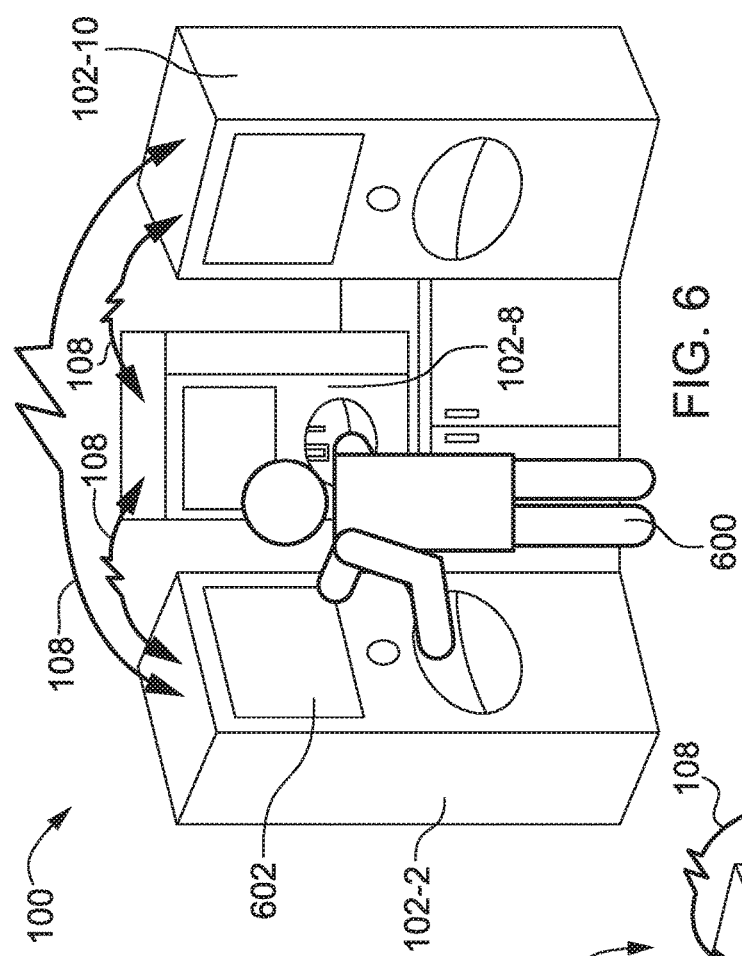
FIG. 6 illustrates an example of communication between beverage vending devices in accordance with various embodiments of beverage vending device networking.
Figure 7:
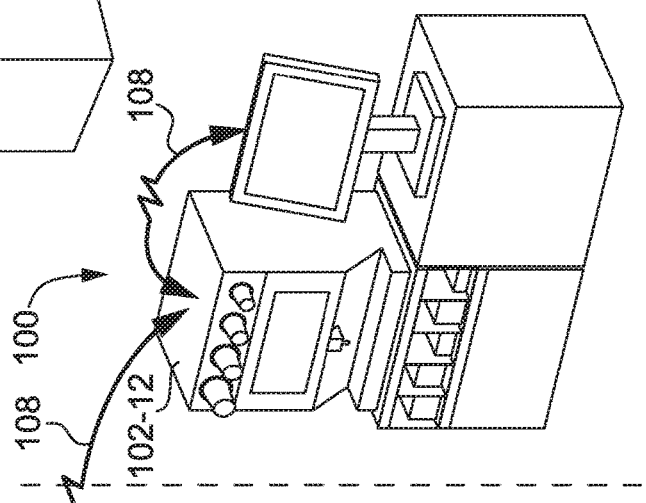
FIG. 7 illustrates an example of communication between beverage vending devices in accordance with various embodiments of beverage vending device networking.

Configuration 100, and its many possible variations, can allow for a wide range of communications among potential devices and entities. FIGS. 5-7 illustrate several such possibilities in accordance with various embodiments of beverage vending device networking. As shown, beverage vending devices 102 can include dispensers of fountain beverages, coolers from which beverages packaged in bottles and cans can be vended, and vending machines from which packaged beverages can be vended. It will be understood that the various configurations of beverage vending devices 102 in FIGS. 5-7 are for illustrative purposes only. For example, more or less beverage vending devices 102 than illustrated may be used. Moreover, any combination of the various types of beverage vending devices 102 may be used, including scenarios in which all of the beverage vending devices 102 are of the same type.

It will also be understood that the beverage vending devices 102 illustrated in FIGS. 5-7 can be networked together directly and/or indirectly using any of the possible embodiments of network 108 in configuration 100 discussed above in FIGS. 1 and 4, including embodiments employing a server 106, even though such a server is not explicitly illustrated in FIG. 5.

For example, FIG. 5 illustrates a possible embodiment of configuration 100 in which three beverage vending devices can exchange information about themselves via network 108. In operation, usage information associated with each beverage vending device 102 can be shared with other beverage vending devices 102 via network 108. For example, if a consumer interacts with a beverage vending device 102 using a particular dispense string 200, information associated with that interaction (i.e. the time it happened, the type of beverage that was vended, the amount of beverage that was vended, the amount of sugar in the beverage that was vended, etc.) can be shared directly and/or indirectly in any of the manners discussed herein with one or more of the other beverage vending devices 102. Thus if the consumer attempts to use dispense string 200 at one of the other beverage vending devices 102 later in an unauthorized manner (i.e. requests a dispense after a designated time period has elapsed from a first dispense/vending of a beverage, and/or tries to get more beverage and/or sugar than might be allowable, etc.) the other beverage vending devices 102 will be able to make appropriate decisions based on what is allowable given the dispense string 200 and the previous beverage vends associated therewith. This can include refusing the dispense being requested by the consumer when it is seen as being unauthorized in light of the consumer's previous interactions with other beverage vending devices 102 on network 108 using dispense string 200.

An example of such a scenario is illustrated in FIG. 6. As shown, a consumer 600 interacting with beverage vending device 102-2 is requesting a particular beverage dispense. In one possible implementation, consumer 600 can present dispense string 200 to beverage vending device 102-2 via any of the scanning and/or input technologies discussed herein, and beverage vending device 102-2 can view information in dispense string 200 in light of any existing interactions with any of the various beverage vending devices 102 on network 108, to determine if the requested dispense is authorized or not. For example, if consumer 600 is requesting a dispense that will put dispense string 200 over a predetermined volume and/or sugar content limit, then beverage vending device 102-2 can refuse the dispense request. Alternately, or additionally, beverage vending device 102-2 can authorize a pour that does not dispense more than the predetermined volume and/or sugar content limit (which can include, for example authorizing a dispense of another beverage, such as water).

In one possible implementation, any information associated with the dispense string 200, such as how much more beverage and/or sugar can be dispensed, what types of beverages can be dispensed, when the dispense string 200 expires, etc., can be presented to consumer 600 via an interface 602 on beverage vending device 102-2. Similarly, previous usage information associated with dispense string 200, consumer information associated with consumer 600, etc., can also be presented on interface 602.

Returning to FIG. 5, beverage vending devices 102 can also communicate inventory information with each other. Inventory information can include, for example, information regarding ingredients, beverages, etc., available at a beverage vending device 102, including the quantities of such ingredients, beverages, etc., that are available. For example, if beverage vending device 102-2 is low on, or out of, ingredients for a particular beverage, this may be communicated to one or more of beverage vending devices 102-4, 102-6. In such a manner, in one possible implementation, the various inventory levels of each beverage vending device 102 may be known by the other beverage vending devices 102 on network 108.

FIG. 7 illustrates a scenario in which consumer 600 interacts with beverage vending device 102-2 and requests a beverage which is out of stock. In such an instance, beverage vending device 102-2 can inform consumer 600 via interface 602 that the beverage being requested is not available on beverage vending device 102-2. Beverage vending device 102-2 can also look at the inventory information it has received from other beverage vending devices 102 and make recommendations on where consumer 600 can go to get the desired beverage. For example, beverage vending device 102-2 can issue a message 704 on interface 602 recommending the consumer to go to a nearby beverage vending device 102-12 at which the requested beverage is available. An example message 704 is illustrated in FIG. 7, however it will be understood that any desired message may be displayed.

Alternately, or additionally, beverage vending device 102-2 can make recommendations on other beverages that consumer 600 may enjoy which are available on beverage vending device 102-2, giving consumer 600 a choice to either go to another beverage vending device 102 for the original beverage requested, or stay at beverage vending device 102-2 where an alternate beverage can be dispensed.

Figure 8:
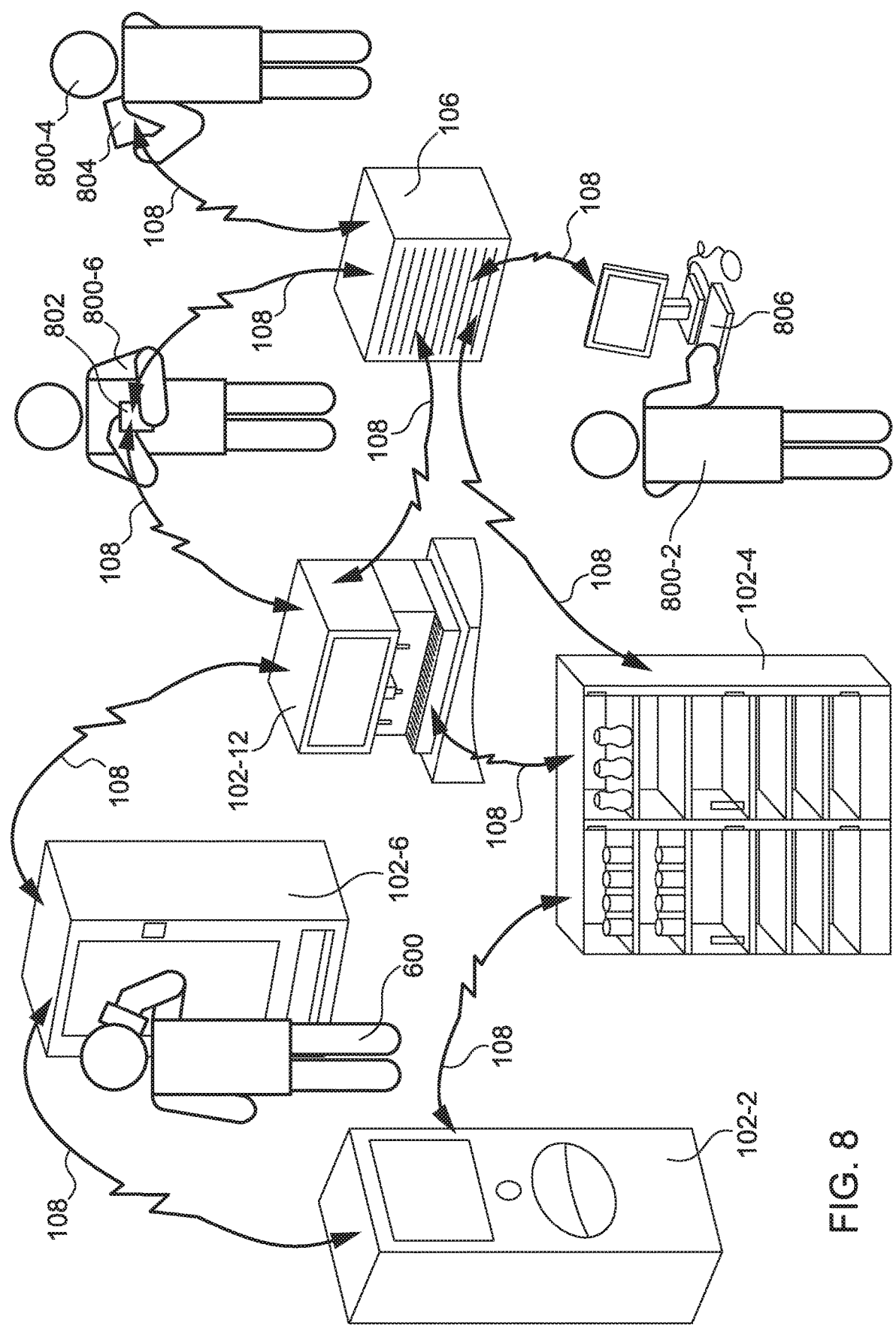
FIG. 8 illustrates an example configuration of one or more beverage vending devices and one or more entities in accordance with various embodiments of beverage vending device networking.

FIG. 8 illustrates an embodiment of configuration 100 in which a plurality of beverage vending devices 102 connected to network 108 can be remotely accessible to various entities 800 wishing to interact with (i.e. monitor, communicate with, etc.) the beverage vending devices 102. Entities 800 can include any entity having an interest in the functioning and/or operation of beverage vending devices 102 including, for example, an operations manager 800-2, a technician 800-4, a manager 800-6 at a seller 104, etc. Entities 800 can interact with beverage vending devices 102 using various computing devices, including a hand held device 802 (such as, for example, a smartphone), a tablet 804, a personal computer 806, a laptop, or any other computing device known in the art. In one possible aspect, entities 800 can interact with beverage vending devices 102 via an app on handled device 802 and/or tablet 804. Further, entities 800 can interact with beverage vending devices 102 directly, and/or indirectly, such as through server 106 and/or one or more other beverage vending devices 102.

For example, in one possible implementation, store manager 800-6 can interact with beverage vending device 102-6 via beverage vending device 102-12. In yet another possible implementation, store manager 800-6 can interact directly with beverage vending device 102-6. In still another possible implementation, store manager 800-6 can interact with beverage vending device 102-6 via server 106. In another possible implementation, store manager 800-6 can interact with beverage vending device 102-6 via server 106 and beverage vending device 102-12.

In one possible implementation, entities 800 can interact with beverage vending devices 102 via one or more internet websites associated with the beverage vending devices 102. In still another possible aspect, various information may be uploaded to a beverage vending device 102 using an internet protocol (IP) address such as file transfer protocol (FTP), or by emailing an account associated with the beverage vending device 102.

In one possible embodiment, beverage vending devices 102-6 can proactively adapt to issues with network 108. For example, if a connection between a given beverage vending device 102 and server 106 is disrupted, the given beverage vending device 102 can begin communicating with server 106 via one or more other beverage vending devices 102 on network 108. This can occur, for example, when the given beverage vending device 102 is scheduled to transmit information such as a periodic report to server 106, but direct communication is not possible. In such an instance the given beverage vending device 102 can make its report to server 106 via one or more other beverage vending devices 102 on network 108. Similar mechanisms can be used to adapt to issues encountered when interaction is desired between an entity 800 and a given beverage vending device 102.

In one possible implementation, any of the possible methods or technologies that entities 800 can use to interact with beverage vending devices 102 and server 106 can be considered to be a portion of network 108.

The information that can be communicated between beverage vending devices 102, server 106, and entities 800 can include anything known in the art, including, for example, any desired usage information associated with one or more or the beverage vending devices 102. Usage information can include any information desirable to an entity 800, including for instance how much of a beverage, ingredient, etc., has been dispensed/vended from one or more beverage vending devices 102, how much of a beverage, ingredient, etc., has been dispensed/vended to individual consumers and/or given dispense strings 200, composite usage information associated with a plurality of beverage vending devices 102, when such dispenses/vendings occurred, etc.

Moreover, the information that can be communicated between beverage vending devices 102, server 106, and entities 800 can include any desired inventory information associated with one or more beverage vending devices 102, such as ingredient levels, product levels, etc.

Further, the information that can be communicated between beverage vending devices 102, server 106, and entities 800 can further include any type of content known in the art. This can include, for example, software, recipes (such as promotional drinks, seasonal recipes, etc.) and any types of updates (such as software updates, menu updates, recipe updates, etc.) of content that may be desired for the one or more beverage vending devices 102.

The information can be communicated between beverage vending devices 102, server 106, and entities 800 using any methodology known in the art. For example, information can be communicated on demand, in real time as events occur, periodically (including at preset times), when an event occurs (such as when an inventory item drops to a predetermined level), etc. Moreover, information can be requested (i.e. pulled) based on the methodology above.

In one possible implementation, the ability to interact with beverage vending devices 102 can enable entities 800 to remotely upload and download information noted herein to and from beverage vending devices 102. For example, individual beverage vending devices 102, can notify one or more of entities 800 of their inventories, including notifying entities 800 when ingredients and/or products get below a preset level. This can allow entities 800 to begin the process of proactively restocking the beverage vending device 102 before the ingredient and/or product goes out of stock. Further, entities 800 can remotely monitor individual beverage vending devices 102 of interest. In one possible implementation, entities 800 can get information on individual beverage vending devices 102 and/or composite information on two or more individual beverage vending devices 102 from server 106. This can include, for example, information allowing a plurality of sellers 104 to accurately divide revenue from sales of beverages to consumers 600 interacting with beverage vending devices 102 (by, for example, using dispense information from beverage vending devices 102, etc.).

Further, individual beverage vending devices 102 can access information from each other, server 106, and entities 800. For instance, consumer information (such as, for example, a consumer profile, etc.) can be accessed from server 106 by a beverage vending device 102 in response to an interaction with the consumer at the beverage vending device 102.

In one possible implementation, entities 800 and server 106 can be termed control entities. In one possible aspect this can arise because of the abilities of entities 800 and server 106 to exert at least partial control over, and effect changes on, various beverage vending devices 102 in some embodiments.

Figure 9:
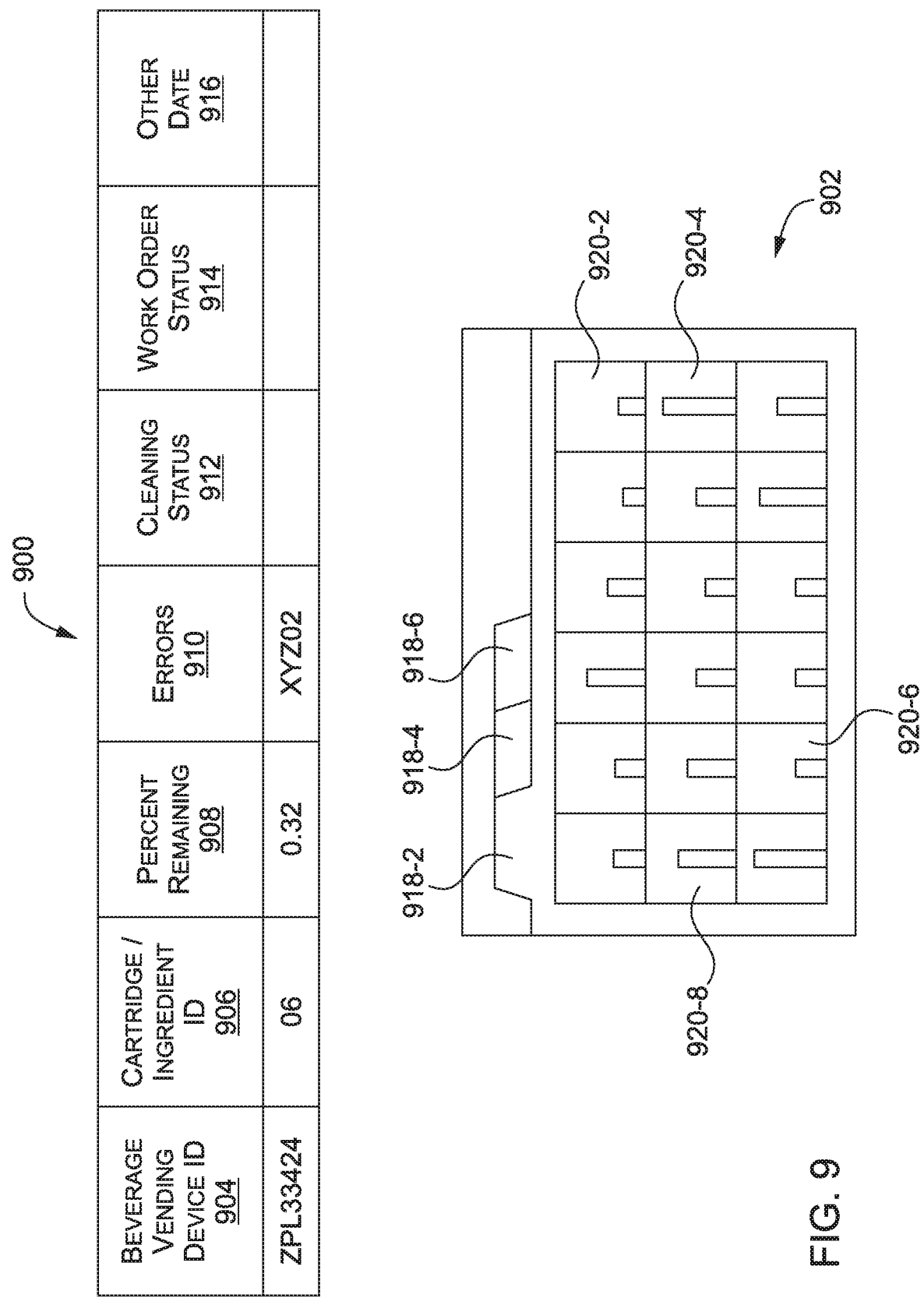
FIG. 9 illustrates example consolidated fuel gauges in accordance with various embodiments of beverage vending device networking.

FIG. 9 illustrates example fuel gauges 900, 902 that can be used to present information associated with one or more beverage vending devices 102 in accordance with embodiments of beverage vending device networking. In one possible implementation, fuel gauges 900, 902, either alone or together, can be presented on the display of any computing device known in the art, including, for example, hand held device 802, a tablet 804, personal computer 806, a laptop, etc., such that entities 800 can view information associated with the one or more beverage vending devices 102 without physically visiting the one or more beverage vending devices 102. Fuel gauges can be implemented through any software known in the art including, for example, through software in a fuel gauge monitor.

As shown, fuel gauge 900 illustrates information associated with a given beverage vending device 102, which can include, for example, an identification (ID) code 904 associated with the given beverage vending device 102. Fuel gauge 900 can also include a cartridge/ingredient ID code 906, an indicator 908 of a percentage remaining of the cartridge/ingredient, as well as a field 910 reporting errors being experienced at the beverage vending device 102. Moreover, fuel gauge 900 can also display a field 912 associated with a cleaning status and a field 914 associated with a work order status of the beverage vending device 102. Additionally a field 916 can exist to display other data of interest to an entity such as, for example, information indicating a software and/or content version, packet data for updates, information associated with a last reboot, etc.

The above content displayed by fuel gage 900 is for illustration only, as it will be understood that more or less content can be displayed on fuel gauge 900 as desired.

Fuel gauge 902 illustrates another possible graphic user interface that can be made available to an entity 800. As illustrated, fuel gauge 902 can include a number of tabs 918, with each tab 918 corresponding to a given beverage vending device 102. For example, if an entity 800 interacting with fuel gauge 902 selects tab 918-2, information associated with a given beverage vending device 102 (such as beverage vending device 102-2) can be displayed, while if entity 800 selects tab 918-4, information associated with another beverage vending device 102 (such as beverage vending device 102-4) can be displayed. The information can be displayed in a plurality of graphic entries 902 which can correspond to anything of interest to an entity, including, for example, fluid levels of cartridges and/or fluid levels of bag in boxes (BIBs), inventories of bottles and/or cans, temperatures, etc., associated with the beverage vending device 102 corresponding to the chosen tab 918. As with fuel gauge 900 above, fuel gauge 902 can be customized to display more or less items of interest in entries 920.

Figure 10:
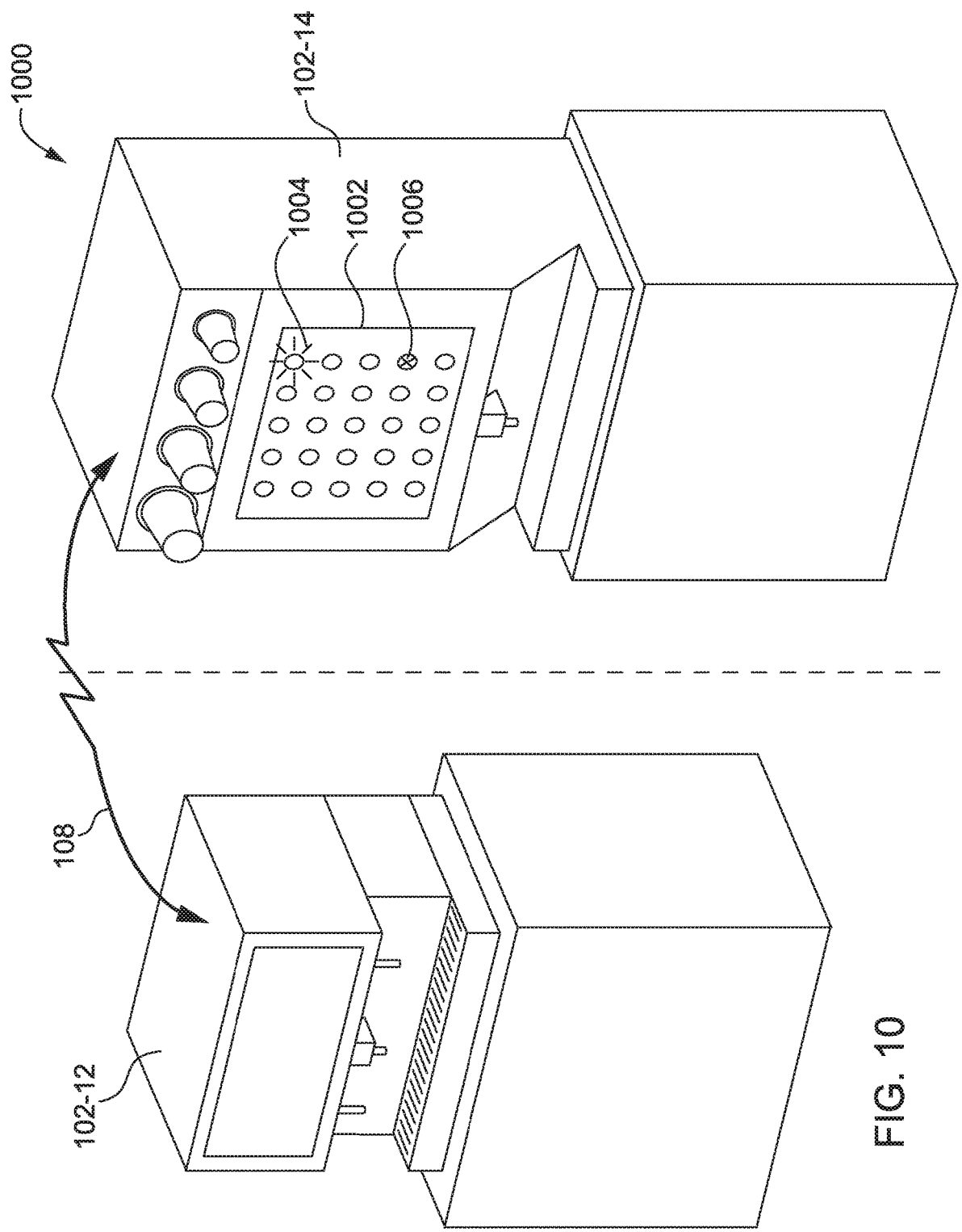
FIG. 10 illustrates an example system for monitoring one or more networked beverage vending devices in accordance with various embodiments of beverage vending device networking.

FIG. 10 illustrates a system 1000 in which a beverage vending device 102-14 can monitor one or more other beverage vending devices 102 on network 108. In one possible embodiment, this can occur in real-time, with beverage vending device 102-14 displaying information such as inventory stock-outs, sold-outs, low ingredient levels, etc., associated with the one or more beverage vending devices 102 being monitored by beverage vending device 102-14. This can occur on a central location such as on a display area 1002 of beverage vending device 102-14, via a stand-alone networked monitor, on a POS screen, and/or via any other desired display device. In one possible implementation, display area 1002 can be located in a back room, at a counter, etc.

In one possible embodiment, any signals/displays known in the art can be used to indicate that ingredients and/or products at the one or more beverage vending devices 102 being monitored are sold out. For example, a flashing light 1004 could indicate that something is sold out in a beverage vending device 102 in a dining room, while an "x" 1006 can indicate that something is sold out on a crew served beverage vending device 102. In a similar fashion, any signals and/or displays known in the art can be employed to indicate that various inventory items, etc. are running low.

Example Method(s)

Figure 11:
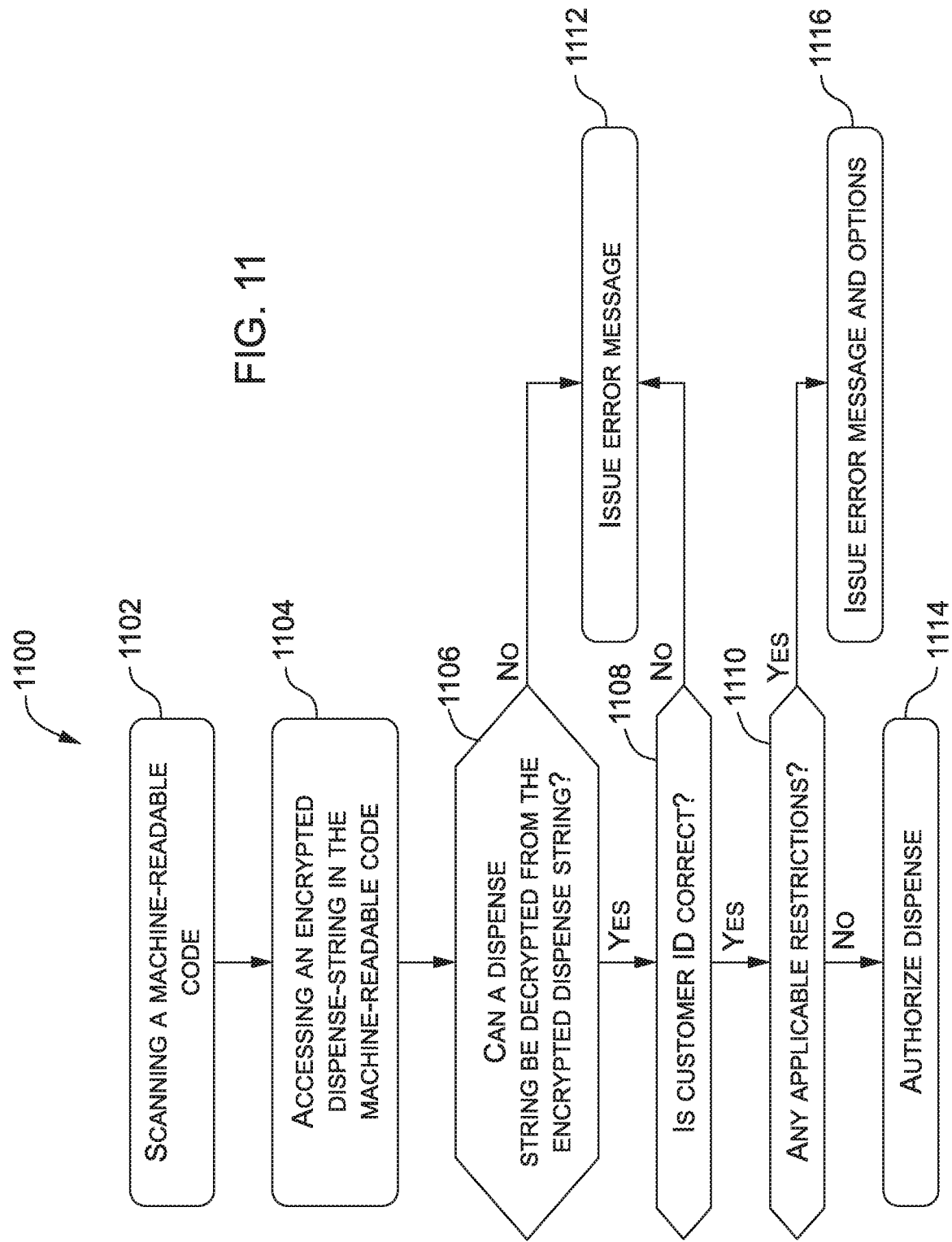
FIG. 11 illustrates example method(s) associated with various embodiments of beverage vending device networking.
Figure 12:
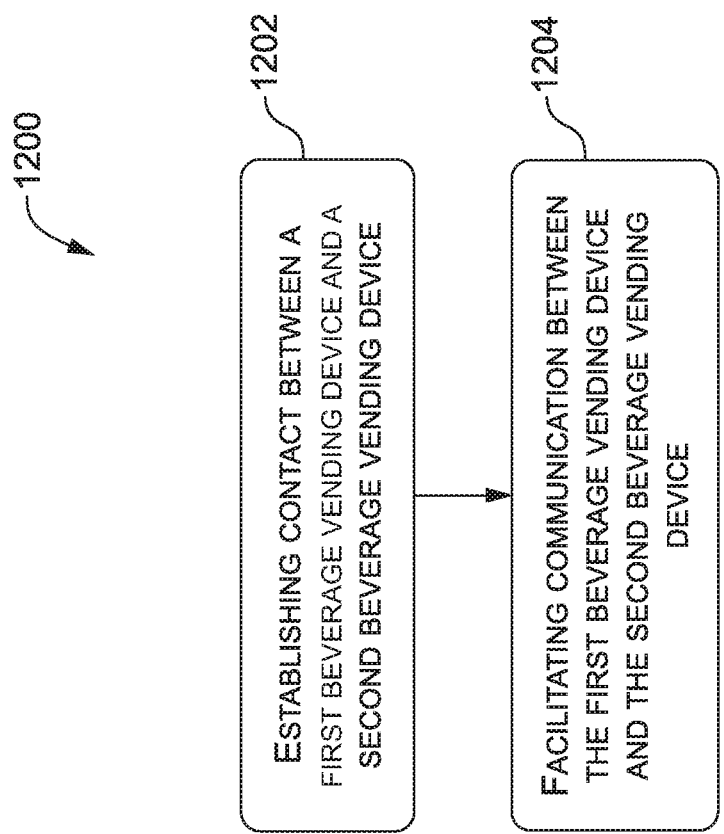
FIG. 12 illustrates example method(s) associated with various embodiments of beverage vending device networking.

FIGS. 11-12 illustrate example methods for implementing aspects of beverage vending device networking. The methods are illustrated as a collection of blocks and other elements in a logical flow graph representing a sequence of operations that can be implemented in hardware, software, firmware, various logic or any combination thereof. The order in which the methods are described is not intended to be construed as a limitation, and any number of the described method blocks can be combined in any order to implement the methods, or alternate methods. Additionally, individual blocks and/or elements may be deleted from the methods without departing from the spirit and scope of the subject matter described therein. In the context of software, the blocks and other elements can represent computer instructions that, when executed by one or more processors, perform the recited operations. Moreover, for discussion purposes, and not purposes of limitation, selected aspects of the methods may be described with reference to elements shown in FIGS. 1-10.

FIG. 11 illustrates example method(s) 1100 for implementing aspects of beverage vending device networking. At block 1102 a machine-readable code, such as for example machine-readable code 212, is scanned. The machine-readable code can be provided to a consumer by a seller, such as seller 104, in response to, for example, a purchase of a beverage by the consumer from the seller. In one possible implementation, the machine-readable code can include anything known in the art, such as, for example, a code associated with a magnetic stripe, a one dimensional barcode, a two dimensional barcode, etc., or any combination thereof. Moreover, the machine-readable code can be issued to the consumer through any technique known in the art. For example, the consumer can receive a cup on which the machine-readable code is printed/formed. Alternately, or additionally, the consumer can receive a receipt, coupon, giftcard, etc., on which the machine-readable code is printed/formed. In one possible implementation, the machine-readable code on such a receipt, coupon, giftcard, etc., can be in the form of a sticker which can be affixed to a beverage container that the consumer can use to receive the desired beverage from a beverage vending device, such as beverage vending device 102. In yet another possible implementation, the machine-readable code can be accessed by the consumer via a handheld device (such as a mobile phone, a tablet, a laptop, etc.) and be displayed on a display of the handheld device.

At block 1104 an encrypted dispense string, such as encrypted dispense string 210, can be accessed. This can include, for example, reading the encrypted dispense string from the machine-readable code. In one possible implementation, this can be implemented by a scanner, such as scanner 114, located anywhere on the beverage vending device. The scanner can include any scanning technologies known in the art configured to scan the machine-readable code and produce the encrypted dispense string.

At block 1106, one or more attempts can be made to decrypt the encrypted dispense string. In one possible aspect, software, such as a decryption module, can be used in such an effort. For example, the beverage vending device can attempt to decrypt the encrypted dispense string using one or more decryption keys, such as decryption keys 112, to produce the underlying dispense string, such as dispense string 200, from the encrypted dispense string.

In one possible implementation, when the dispense string has been encrypted using a private key, a decryption module can decrypt the encrypted dispense string using a corresponding public key, such as might be stored in an encryption/decryption key(s) memory location. In one possible aspect, a keyring of multiple public keys can be available in the encryption/decryption key(s) memory location, such that the decryption module can try several public keys before finding the proper public key associated with the private key used to encrypt the dispense string into the encrypted dispense string.

In one possible implementation, when the encrypted dispense string is decrypted, method 1100 can move to block 1108 where a customer identifier (ID), such as customer ID 202, in the dispense string can be checked against the public key used for the decryption. In one possible aspect, if the public key is appropriate for the customer ID (i.e. the customer ID and the public key are both associated with the same seller), the dispense string can be processed as a valid string and method 1100 can move on to block 1110. If not, the next public key on the keyring can be checked until a valid customer ID 202-public key pair is found or until all the public keys have been tried.

If no matching decryption key is found, in one possible embodiment, the encrypted dispense string will not be decrypted by the decryption module, and method 1100 can proceed to block 1112. Alternately, or additionally, if the public key is not appropriate for the customer ID (i.e. the customer ID and the public key are not both associated with the same seller), method 1100 can proceed from block 1108 to block 1112.

At block 1112, the beverage vending device can issue any desirable error message, such as, for example, that the machine-readable code is incorrect. The beverage vending device can also display a try again strategy with instructions on how to reenter the machine-readable code into the scanner on the beverage vending device. In one possible implementation, error messages, instructions, etc., can be displayed on a display, such as interface 602, associated with the beverage vending device.

At block 1110, if a matching decryption key is found, and the customer ID is correct, at least some of the dispense string may be used to determine allowable dispense options. In one possible implementation this can include determining if any restrictions stand in the way of a particular beverage dispense. Such restrictions can result in the alteration or cancellation of a requested beverage dispense Restrictions that can be used to constrain allowable dispense options can include anything desirable to the seller and/or a person or entity, such as entities 800, administering the beverage vending device including, for example, restrictions on refills, restrictions on a time during which beverage dispenses can be made, restrictions on an amount of sweetener dispensed to the consumer in a given period of time, restrictions on an amount of calories dispensed to the consumer in a given period of time, restrictions on a type of beverage that can be dispensed to the consumer given the type of beverage purchased by the consumer (i.e. purchases of water may not be eligible for beverage dispenses of more expensive beverages like juices), etc. In one possible implementation, some or all of the restrictions applicable to a beverage vending device can be stored in a restrictions area in memory. Moreover, the restrictions, and their limits and thresholds, etc., can be updated through communications between multiple beverage vending devices (such as beverage vending devices 102-2, 102-4, 102-6, for example) and/or between the beverage vending device and one or more outside entities, including for example, a server (such as server 106), and the seller, etc.

For example, in some jurisdictions, laws and/or regulations may exist stipulating a restriction that no refills be given of certain beverages. In another possible example, laws and/or regulations may exist stipulating restrictions associated with a maximum limit of calories and/or sugar that can be dispensed in one or more beverages to a consumer in a given time period. In yet another possible example, a restriction may exist regarding a duration of validity of the dispense string (i.e. a validity period, such as validity period 204, during which the consumer may request a beverage dispense). The duration of validity can be, for example, a given calendar day, a set number of hours from the purchase of the beverage from the seller, and/or within any other time limit set by the seller and/or the entity administering the beverage vending devices.

In one possible aspect, if a beverage dispense requested by a customer associated with the dispense string doesn't run afoul of any of the restrictions (i.e. the beverage dispense requested by the customer is within the allowable dispense options associated with the dispense string), method 1100 can proceed to block 1114 and a beverage dispense decision can be made to implement the requested beverage dispense. In one possible embodiment, the beverage dispense can be made from the beverage vending device at which the beverage dispense request is being made by the customer.

In another possible aspect, if the beverage dispense requested by the consumer associated with the dispense string runs afoul of any of the restrictions, method 1100 can proceed to block 1116 where a beverage dispense decision can be made to either issue an error message and block the requested beverage dispense, or issue an error message and present the consumer with a few options (if any are possible) on how to vary the requested beverage dispense requested to avoid running afoul of the restriction(s).

FIG. 12 illustrates example methods 1200 for implementing aspects of beverage vending device networking. At block 1202 contact is established between a first beverage vending device and a second beverage vending device. In one possible implementation, the first beverage vending device and the second beverage vending device can take any of the forms of a beverage vending device 102 (i.e., beverage dispensers—such as dispensers of fountain beverages, etc., vending machines, coolers, etc.).

The first beverage device can be part of a configuration of beverage vending devices, such as configuration 100, and can establish contact with the second beverage vending device using any of the possible methods associated with configuration 100, through a network, such as network 108. For example, in one possible implementation, the first beverage vending device can establish contact with the network and then locate the second beverage vending device on the network. In another possible implementation, the first beverage vending device can simply begin broadcasting and receive an answer from the second beverage vending device.

At block 1204, communication can be facilitated between the first beverage vending device and the second beverage vending device using any techniques associated with configuration 100. This can include, for example, indirect communication, in which the first beverage vending device communicates with the second beverage vending device through a backend server, such as server 106 and/or through one or more other beverage vending device.

In another possible implementation, communication between the first beverage vending device and the second beverage vending device can occur directly, such as, through a direct connection between the first beverage vending device and the second beverage vending device.

Any information desired can be communicated between the first beverage vending device and the second beverage vending device, including inventory information, usage information, update information, software updates, etc.

Example Computing Device(s)

Figure 13:
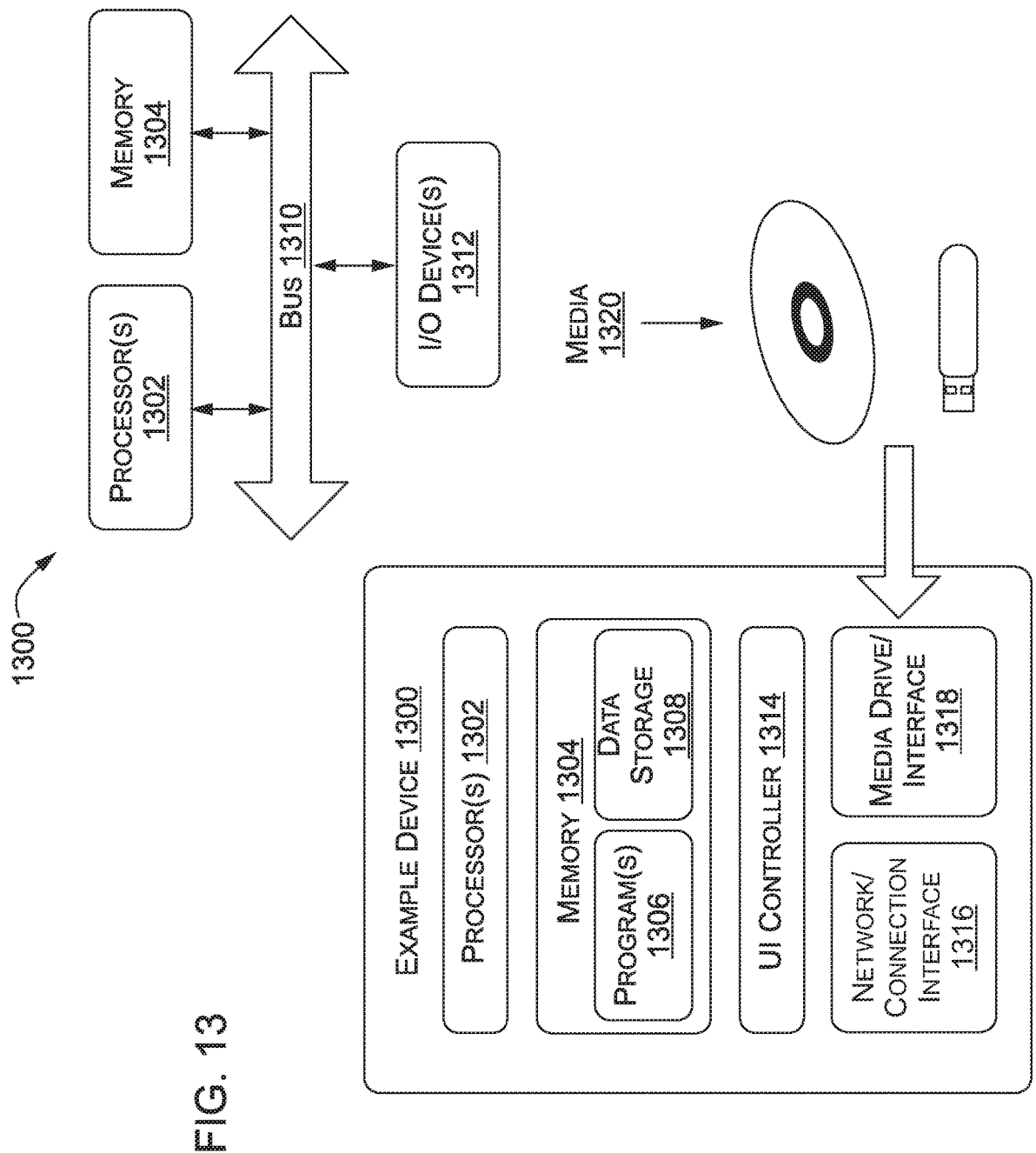
FIG. 13 illustrates an example computing device that can be used in accordance with various implementations of beverage vending device networking.

FIG. 13 illustrates an example device 1300, with one or more processor(s) 1302 and memory 1304 for hosting programs 1306 configured to implement various embodiments of beverage vending device networking as discussed in this disclosure.

Memory 1304 can also host data storage 1308 such as, for example, one or more databases, and a variety of data discussed herein. Memory 1304 can comprise one or more forms of volatile data storage media such as random access memory (RAM), and/or one or more forms of nonvolatile storage media (such as read-only memory (ROM), flash memory, and so forth).

Device 1300 is one example of a computing device or programmable device, and is not intended to suggest any limitation as to scope of use or functionality of device 1300 and/or its possible architectures. For example, device 1300 should not be interpreted as having any dependency relating to one or a combination of components illustrated in device 1300. Device 1300 can comprise one or more desktop computers, programmable logic controllers (PLCs), laptop computers, handheld devices, mainframe computers, computing clusters, clouds, etc., including any combination or accumulation thereof. Further, one or more devices 1300 can be included in beverage vending devices 102 and be used to provide the functionality described herein.

Device 1300 can also include a bus 1310 configured to allow various components and devices, such as processors 1302, memory 1304, and local data storage among other components, to communicate with each other.

Bus 1310 can include one or more of any of several types of bus structures, including a memory bus or memory controller, a peripheral bus, an accelerated graphics port, and a processor or local bus using any of a variety of bus architectures. Bus 1310 can also include wired and/or wireless buses.

Data storage 1308 can include local data storage such as fixed media (e.g., RAM, ROM, a fixed hard drive, etc.) as well as removable media (e.g., a flash memory drive, a removable hard drive, optical disks, magnetic disks, and so forth), cloud storage, etc.

One or more input/output (I/O) device(s) 1312 may also communicate via a user interface (UI) controller 1314, which may connect with I/O device(s) 1312 either directly or through bus 1310.

In one possible implementation, a network/connection interface 1316 may communicate outside of device 1300 via a connected network (such as network 108, for example), and in some implementations may communicate with hardware such as various functionality found in a beverage vending device 102, etc. Network/connection interface 1316 can include any device configured to send and/or receive electronic signals, including, for example, modems, three in one connectivity modules, etc.

In one possible embodiment, communication between device 1300 and functionality in a beverage vending device 102 and/or consumers interacting with the beverage vending device and/or one or more remote servers 106, etc., can be facilitated through input/output device(s) 1312 via bus 1310, such as via a USB port, for example.

A media drive/interface 1318 can accept removable tangible media 1320, such as flash drives, optical disks, removable hard drives, software products, etc.

In one possible embodiment, input/output device(s) 1312 can allow a consumer to enter commands and information to device 1300, and also allow information to be presented to the consumer and/or other components or devices. Examples of input device(s) 1312 include, for example, sensors, scanners (such as scanners 114), a keyboard, a touch screen display, a cursor control device (e.g., a mouse), a microphone, and any other input devices known in the art. Examples of output devices include a display device (e.g., a monitor or projector), speakers, a printer, a network card, and so on.

Various processes of programs 1306 may be described herein in the general context of software or program modules, or the techniques and modules may be implemented in pure computing hardware. Software generally includes routines, programs, objects, components, data structures, and so forth that perform particular tasks or implement particular abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and nonvolatile, removable and non-removable tangible media implemented for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information, and which can be accessed by a computer.

In one possible implementation, device 1300, or a plurality thereof, can be employed within one or more beverage vending devices, seller terminals, remote servers, etc.

Figure 14:
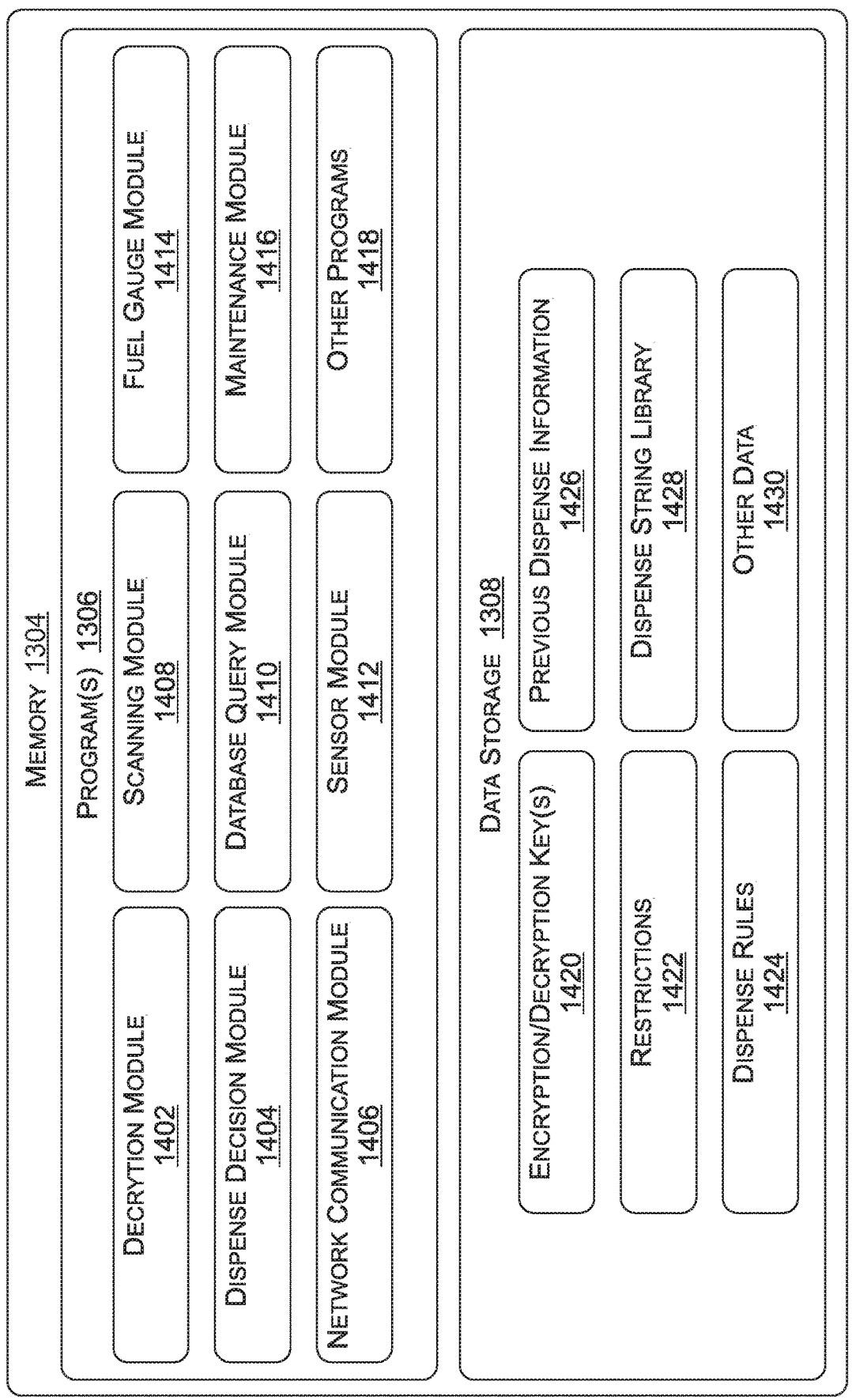
FIG. 14 illustrates example programs and data that can be used in accordance with various implementations of beverage vending device networking.

FIG. 14 illustrates an example configuration of memory 1304 comprising computer-readable media including programs 1306 and data storage 1308 configured to implement various embodiments of beverage vending device networking as discussed in this disclosure. Memory 1304 can provide any storage mechanisms known in the art to store various information, data and/or instructions such as program(s) 1306 (including any types of software known in the art) and any other types of information and data related to operational aspects of device 1300. For example, programs 1306 stored in memory 1304 can include a decryption module 1402, a dispense decision module 1404, a network communication module 1406, a scanning module 1408, a database querying module 1410, a sensor module 1412, a fuel gauge module 1414, a maintenance module 1416 and other modules that are not shown in FIG. 14, such as a point of sale (POS) module, an order management module, etc. Programs 1306 stored in memory 1304 can also include other programs 1418—such as an operating system and/or assorted application programs. Programs 1306 can be executed on processor(s) 1302.

Memory 1304 can also include data storage 1308 in which can be stored, for example, information such as encryption keys and/or decryption keys 1420 (including encryption keys 110, decryption keys 112, one or more private keys and/or one or more public keys), restrictions 1422, dispense rules 1424, previous dispense information 1426, a dispense string library 1428, and other data 1430 (including intermediate and final data created through use of one or more programs 1306).

Any of programs 1306 and data in data storage 1308 can reside wholly or partially on any of a variety of media types found in memory 1304 and/or media 1320. For example, portions of decryption module 1402 can reside at different times in random access memory (RAM), read only memory (ROM), optical storage discs (such as media 1320), cloud memory, optical devices, flash devices, etc. Alternately, or additionally, some or all of program(s) 1306 may be implemented through use of other functionality, such as electronic circuitry, etc.

Although a few example embodiments have been described in detail above, those skilled in the art will readily appreciate that many modifications are possible in the example embodiments without materially departing from this disclosure. Accordingly, such modifications are intended to be included within the scope of this disclosure as defined in the following claims. Moreover, embodiments may be performed in the absence of any component not explicitly described herein.

In the claims, means-plus-function clauses are intended to cover the structures described herein as performing the recited function and not just structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, using "and" or "or" is intended to include "and/or" unless specifically indicated otherwise. The illustrative embodiments may be implemented as a method, apparatus, or article of manufacture using standard engineering techniques.

What is claimed is:

1. A beverage vending device comprising:
   a network interface;
   one or more processors; and
   a computer-readable tangible medium with instructions stored thereon that, when executed, direct the one or more processors to perform acts comprising:
      establishing contact with a second beverage vending device on an available network;
      receiving inventory information associated with the second beverage vending device;
      receiving a request from a consumer to dispense a desired beverage;
      determining that the desired beverage cannot be dispensed by the beverage vending device;
      utilizing the inventory information to determine that the second beverage vending device can dispense the desired beverage;
      providing the consumer a choice to either go to the second beverage vending device to request a dispense of the desired beverage or stay at the beverage vending device and choose an alternate beverage to be dispensed;
      receiving a second request from the consumer to dispense a second beverage; and
      instructing the beverage dispensing device to dispense the second beverage.

2. The beverage vending device of claim 1, wherein the beverage vending device comprises one or more of:
   a beverage dispenser;
   a cooler;
   a vending machine.

3. The beverage vending device of claim 1, wherein the computer-readable tangible medium further includes instructions to direct the one or more processors to perform acts comprising:
   communicating with a control entity via the second beverage vending device.

4. The beverage vending device of claim 1, wherein the computer-readable tangible medium further includes instructions to direct the one or more processors to perform acts comprising:
   accessing information associated with the beverage vending device; and
   communicating the information associated with the beverage vending device to one or more of:
      a control entity;
      a server;
      the second beverage vending device.

5. The beverage vending device of claim 4, wherein the computer-readable tangible medium further includes instructions to direct the one or more processors to perform acts comprising:
   accessing information associated with the beverage vending device comprising one or more of:
      inventory information associated with beverage ingredients at the beverage vending device;
      usage information associated with the beverage vending device.

6. The beverage vending device of claim 1, wherein the computer-readable tangible medium further includes instructions to direct the one or more processors to perform acts comprising:
   receiving one or more updates via the network.

7. The beverage vending device of claim 1, further comprising a scanner, and further wherein the computer-readable tangible medium further includes instructions to direct the one or more processors to perform acts comprising:
   receiving via the scanner an encrypted dispense string encrypted by an encryption key;
   decrypting the encrypted dispense string with a decryption key to produce a dispense string; and
   concluding a beverage dispense decision based at least in part on a string serial number in the dispense string.

8. A computer-readable tangible medium configured for use with a first beverage vending device, the computer-readable tangible medium including instructions stored thereon that, when executed, direct a processor to perform acts comprising:
   establishing contact between the first beverage vending device and a second beverage vending device;
   facilitating communication between the first beverage vending device and the second beverage vending device;
   accessing inventory information associated with the second beverage vending device;
   receiving a request from a consumer to dispense a desired beverage;
   determining that the desired beverage cannot be dispensed by the first beverage vending device;
   utilizing the inventory information to determine that the second beverage vending device can dispense the desired beverage;
   informing the consumer that the desired beverage is not available at the first beverage dispensing device and that the desired beverage is available for dispense at the second beverage vending device, and recommending to the consumer one or more other beverages available at the first beverage vending device;
   receiving a second request from the consumer to dispense a second beverage; and
   instructing the first beverage dispensing device to dispense the second beverage.

9. The computer-readable tangible medium of claim 8, further including instructions to direct a processor to perform acts comprising:
   facilitating contact between the first beverage vending device and a control entity.

10. The computer-readable tangible medium of claim 9, further including instructions to direct a processor to perform acts comprising:
   facilitating contact between the first beverage vending device and the control entity at least partially via the second beverage device.

11. The computer-readable tangible medium of claim 8, further including instructions to direct a processor to perform acts comprising:
   accessing information associated with the first beverage vending device; and
   communicating the information associated with the first beverage vending device to one or more of:
      a control entity;
      a server;
      the second beverage vending device.

12. The computer-readable tangible medium of claim 8, further including instructions to direct a processor to perform acts comprising:
   receiving updates at the first beverage vending device via a network.

13. The computer-readable tangible medium of claim 8, further including instructions to direct a processor to perform acts comprising:
   transmitting information associated with the first beverage device to a control entity.

14. The computer-readable tangible medium of claim 8, further including instructions to direct a processor to perform acts comprising:
   accessing an encrypted dispense string presented by a consumer to the first beverage vending device, wherein the encrypted dispense string has been encrypted by an encryption key;
   accessing a beverage dispense request input by the consumer to the first beverage vending device;
   decrypting the encrypted dispense string with a decryption key to produce a dispense string; and
   utilizing information associated with a string serial number in the dispense string to conclude a beverage dispense decision with regard to the beverage dispense request.

15. A beverage vending device comprising:
   a network interface;
   one or more processors; and
   a computer-readable tangible medium with instructions stored thereon that, when executed, direct the one or more processors to perform acts comprising:
      locating a second beverage vending device;
      establishing communication with the second beverage vending device accessing inventory information associated with the second beverage vending device;
      receiving a request from a consumer to dispense a desired beverage at the beverage dispensing device;
      determining that the desired beverage cannot be dispensed by the beverage vending device;
      utilizing the inventory information to determine that desired beverage can be dispensed by the second beverage vending device;
      informing the consumer that the desired beverage is not available at the beverage dispensing device and that the desired beverage is available for dispense at the second beverage vending device, and recommending to the consumer one or more other beverages available at the beverage vending device.

16. The beverage vending device of claim 15, wherein the beverage vending device comprises one or more of:
   a beverage dispenser;
   a cooler;
   a vending machine.

17. The beverage vending device of claim 15, wherein the computer-readable tangible medium further includes instructions to direct the one or more processors to perform acts comprising:
   accessing information associated with the beverage vending device; and
   communicating the information associated with the beverage vending device to the second beverage vending device.

18. The beverage vending device of claim 15, further including a scanner, and further wherein the computer-readable tangible medium further includes instructions to direct the one or more processors to perform acts comprising:
   allowing a consumer to input an encrypted dispense string via the scanner, wherein the encrypted dispense string has been encrypted using a private key;

decrypting the encrypted dispense string using a public key to produce a dispense string; and determining one or more allowable dispense options associated with the dispense string.

* * * * *